US006541615B1

(12) United States Patent
Ullrich et al.

(10) Patent No.: US 6,541,615 B1
(45) Date of Patent: Apr. 1, 2003

(54) SIRP PROTEINS AND USES THEREOF

(75) Inventors: Axel Ullrich, München (DE); Alexei Kharitonenkov, Carmel, IN (US); Zhengiun Chen, Graefelfing (DE)

(73) Assignee: Max-Planck-Gellschaft zur Foderung der Wissenschaften E.V., Munich (DE)

( * ) Notice: Subject to any disclaimer, the term of this patent is extended or adjusted under 35 U.S.C. 154(b) by 0 days.

(21) Appl. No.: 08/999,689

(22) Filed: Nov. 14, 1997

Related U.S. Application Data

(60) Provisional application No. 60/030,964, filed on Nov. 15, 1996.

(51) Int. Cl.$^7$ .............................................. C07H 21/02
(52) U.S. Cl. ................ 536/23.1; 536/23.1; 536/23.6; 530/300; 530/350; 435/6; 435/7.1; 435/172.3; 435/320.1; 435/325; 800/205
(58) Field of Search .................. 435/6, 7.1, 172.3, 435/320.1, 325; 530/350, 300; 800/205; 536/23.6, 23.1

(56) References Cited

U.S. PATENT DOCUMENTS

| | | | |
|---|---|---|---|
| 4,945,050 A | 7/1990 | Sanford et al. | ........... 435/172.1 |
| 5,283,173 A | 2/1994 | Fields et al. | .................... 435/6 |
| 5,530,186 A | * 6/1996 | Hitz et al. | ................... 800/205 |

FOREIGN PATENT DOCUMENTS

| | | |
|---|---|---|
| WO | WO 93/09236 | 5/1993 |
| WO | WO 94/23039 | 10/1994 |
| WO | WO 97/35019 | 9/1997 |
| WO | WO97/48723 | * 12/1997 |

OTHER PUBLICATIONS

Kharltonenkov et al., Nature, vol. 386(6621), pp. 181–186, 1997.*
Berry et al., Nature Genetics, vol. 10, pp. 415–423, Aug. 1995.*
Margolis et al., Somatic Cell and Molecular Genetics, vol. 21, No. 4, pp. 279–284, 1995.*
Cross et al., Nature Geneticess, vol. 6, pp. 236–244, Mar. 1994.*
Alignments, Direct Submission, 1995.*
Wu et al., "Molecular Cloning of a Transcriptional Repressor Protein (SIRP-1) Which Binds to the Intestine–Specific Promoter Region of the Sucrase–Isomaltase Gene," 94$^{th}$ Annual Meeting of the American Gastroenterological Association, Boston, May 15–21, 1993.
Wu et al., "Molecular Cloning of a Transcriptional Repressor Protein (SIRP-1) Which Binds to the Intestine–Specific Promoter Region of the Sucrase–Isomaltase Gene," *Gastroenterology* 104(4, part 2):A290 abstract (1993).
EMBI Acession No. U49853, "Mus Musculus Protein Tyrosine Phosphatase, mRNA, Complete cds." Mar. 27, 1996.
EMBL Accession number U55057, Rel. 47 created on May 28, 1996 Mus musculus receptor protein tyrosine phosphatase–lambda (ptp–lambda) mRNA. XP002064044 see the whole document.
Izaki, et al., Heavy Metal Resistance Of Plasmids, Japanese Journal of Bacteriology vol. 33 No. 6, Nov. 1978.
Ausubel et al., Current Protocols in Molecular Biology, *Greene Publishing Associates and Wiley Interscience, NY* (1989) (Table of Contents Only).
Barford et al., "Crystal Structure of Human Protein Tyrosine Phosphatase 1B," *Science* 263:1397–1403 (1994).
Bayer et al., "The Avidin–Biotin Complex in Affinity Cytochemistry," *Methods in Enzymol,* 62:308–319 (1979).
Beckman et al., "An Adhesive Domain Detected in Functionally Diverse Receptors", *Trends Biochem. Sci.* 18:40–41 (1993).
Ben–David et al., "A Mammalian Protein Kinase with Potential for Serine/Threonine and Tyrosine Phosphorylation is Related to Cell Cycle Regulators" *EMBO J.* 10(2) 317–325 (1991).
Benoist et al., "In Vivo Sequence Requirements of the Sv40 Early Promoter Region," *Nature* 290, 304–310 (1981).
Blaschuk et al., "Identification of a Conserved Region Common to Cadherins and Influenza Strain A Hemagglutinins" *J. Mol. Biol.* 211, 679–682 (1990).
Bollon et al., "DNA Transformation Efficiency of Various Bacterial and Yeast Host–Vector Systems," *Journal of Clinical Hematology and Oncology* 10(2&3):39–48 (1980).
Botstein et al., "Maldng Mutations in vitro and Putting Them Back into Yeast," *Academic Press,* 19, 265–274 (1982).
Brinster et al., "Factors Affecting the Efficiency of Introducing Foreign DNA into Mice by Microinjecting Eggs," *Proc. Natl. Acad. Sci., USA* 82:4438–4442 (1985).
Broach, "The Yeast Plasmid 2$\mu$ Circle," in *The Molecular Biology of the Yeast Saccharomyces: Life Cycle and Inheritance,* Cold Spring Harbor Laboratory, Cold Spring Harbor, NY, pp. 445–470 (1981).
Broach, "The Yeast Plasmid 2$\mu$ Circle," *Cell* 28:203–204 (1982).
Brown–Shimer et al., "Molecular cloning and chromosome mapping of the human gene encoding protein phosphotyrosyl phosphatase 1B," *Proc. Natl. Acad. Sci. USA* 87:5148–5152 (1990).
Bullock et al., "Techniques in Immunocytochemistry," vol. 1 (1982), vol. 2 (1983), vol. 3 (1985) (Table of Contents Only).
Campbell, "Monoclonal Antibody Technology: Laboratory Techniques in Biochemistry and Molecular Biology," 13, (1984) (Table of Contents Only).

(List continued on next page.)

Primary Examiner—Karen Cochrane Carlson
Assistant Examiner—Hope A. Robinson
(74) Attorney, Agent, or Firm—Foley & Lardner

(57) ABSTRACT

The present invention features isolated, purified, or enriched nucleic acid encoding a SIRP polypeptide and isolated, purified, or enriched SIRP polypeptide and uses thereof.

17 Claims, 3 Drawing Sheets

OTHER PUBLICATIONS

Capecchi, "Altering the Genome by Homologous Recombination," *Science* 244(1) 1288–1292 (1989).

Capecchi, "High Efficiency Transformation by Direct Microinjection of DNA into Cultured Mammalian Cells," *Cell* 22:479–488 (1980).

Cenatiempo, Prokaryotic gene expression in vitro: transcription–translation coupled systems, *Biochimie* 68, 505–515 (1986).

Chao, "Growth Factor Signaling: Where is the Specificity?" *Cell* 68:995–997 (1992).

Chard, "An Introduction to Radioimmunoassay and Related Techniques," *Elsevier Science* (1986) (Table of Contents Only).

Chater et al., "Streptomyces φC3 1–Like Phages: Cloning Vectors, Genome Changes and Host Range," *Sixth International Symposium on Actinomycetes Biology*, 45–52 (1986).

Chirgwin et al., "Isolation of Biologically Active Ribonucleic Acid from Sources Enriched in Ribonuclease" *Biochemistry* 18, 5294–5299 (1979).

Chu et al., "Etectroporation for the Efficient Transfection of Mammalian Cells with DNA," *Nucl. Acids Res.* 15(3) 1311–1326 (1987).

Ciossek et al, "Cloning, Characterization, and Differential Expression of MDK2 and MDK5, Two Novel Receptor Tyrosine Kinases of the eck/eph Family" *Oncogene* 11:2085–2095 (1995).

Colwill et al., "The Clk/Sty Protein Kinase Phosphorylates SR Splicing Factors and Regulates Their Intranuclear Distribution" *EMBO J.* 15:265–275 (1996).

Cool et al., "DNA Isolated from a Human T–cell Library Encodes a Member of the Protein–tyrosine–phosphatase Family," *Proc. Natl. Acad. Sci. USA* 86, 5257–5761 (1989).

Cunningham et al., "Neural Cell Adhesion Molecule: Structure, immunoglobulin–Like Domains, Cell Surface Modulation, and Alternative RNA Splicing" *Science* 236, 799–806 (1987).

Curiel et al., "Gene Transfer to Respiratory Epithelial Cells via the Receptor–mediated Endocytosis Pathway," *Am. J. Respir. Cell. Mol. Biol.* 6, 247–252(1992).

Dignam et al., "Accurate Transcription Initiation by RNA Polymerase II in a Soluble Extract from Isolated Mammalian Nuclei," *Nucl. Acids Res.* 11(5) 1475–1489 (1983).

Dingwall et al., "Nuclear Targeting Sequences a Consensus?" *TIBS* 16, 478–481(1991).

Dreborg et al., "Ch. 10—The chemistry and standardization of allergens," *Handbook of Experimental Immunology—Volume 1: Immunochemistry, 4th Ed., Blackwell Scientific Publications*, 10, 10.1–10.28 (1986).

Duncan et al., "Alternative Splicing of STY, a Nuclear Dual Specificity Kinase" *J. Biol. Chem.* 270:21524–21531 (1995).

Eaton et al., "Construction and Characterization of an Active Factor VIII Variant Lacking the Central One–Third of the Molecule" *Biochemistry* 25(26) 8343–8347 (1986).

Engvall et al., "Enzyme–Linked Immunosorbent Assay, ELISA. III. Quantitation of Specific Antibodies by Enzyme–Labeled Anti–Immunoglobulin in Antigen–Coated Tubes," *J. Immunol.* 109, 129–135 (1972).

Felgner et al., "Lipofection: A Highly Efficient, Lipid–mediated Dna–transfection Procedure," *Proc. Natl. Acad. Sci. USA* 84:7413–7417(1987).

Felgner et al., "Cationic Liposome–mediated Transfection," *Nature* 337, 387–388 (1989).

Field et al., Cloning and Characterization of CAP, the *S. Cerevisiae* Gene Encoding the 70 kd Adenylyl Cyclase–Associated Protein *Cell* 61:319–327 (1990).

Flores et al., "Nuclear Localization of sthe PEP Protein Tyrosine Phosphatase" *Mol. Cell. Biol.* 14:4938–4946 (1994).

Garton et al., A.J. and Tonics, N.K., PTP–PEST: a protein tyrosine phosphatase regulated by serine phosphorylation. *EMBO J.* 13:3763–3771 (1994).

Gilman et al., "Isolation of sigma–28–specific promoters from *Bacillus subtilis* DNA," *Gene* 32, 11–20(1984).

Glick et al., "Factors affecting the expression of foreign proteins in *Escherichia coli*," *Journal of Industrial Microbiology* 1,277–282 (1987).

Goding, "Conjugation of Antibodies with Fluorochromes: Modifications to the Standard Methods," *J. Immunological Methods* 13:215–226 (1976).

Gold et al., "Translational Initiation in Prokaryotes," *Ann. Rev. Microbiol.* 35:365–403 (1981).

Gottesman, "Bacterial Regulation: Global Regulatory Networks," *Ann. Rev. Genet.* 18, 415–441 (1984).

Hamer et al., "Regulation In Vivo of a Cloned Mammalian Gene: Cadmium Induces the Transcription of a Mouse Metallothionein Gene in SV40 Vectors," *J. of Mol. and Applied Genetics* 1, 273–288 (1982).

Hammer et al., "Spontaneous Inflammatory Disease in Transgenic Rats Expressing HLA–B27 and Human $\beta_2$m: An Animal Model of HLA–B27–Associated Human Disorders," *Cell* 63, 1099–1112 (1990).

Hedley et al., "An Amino Acid Sequence Motif Sufficient for Subnuclear Localization of an Arginine/Serine–rich Splicing Factor" *Proc. Natl. Acad. Sci. USA* 92:11524–11528 (1995).

Houdebine et al., "Transgenesis in Fish," *Experientia* 47, 891–897 (1991).

Howell et al., "STY, a Tyrosine–Phosphoprylationing Enzyme with Sequence Homology to Serine/Threonine Kinases" *Mol and Cell Biol.* 11(1) 568–572 (1991).

Hurby et al., "Applications of Synthetic Peptides: Antisense Peptides" in *Synthetic Peptides: A User's Guide*, edited by Gregory A. Grant, W.H. Freeman, NY, pp. 289–307 (1992).

Innis et al., "A Guide to Methods and Applications," Academic Press (1990) (Table of Contents Only).

Izaki, *Jpn J. Bacteriol.* 33:729–742 (1978).

Jasny, "Insect Viruses Invade Biotechnology," *Science* 238, p. 1653 (1987).

Jiang et al., "The α Subunit of Merpron A . . . " *J. of Biol. Chem.* 267:9185–9193 (1992).

John et al., "Plasmids as Epidemiologic Markers in Nosocomial Gram–Negative Bacilli: Experience at a University and Review of the Literature," *Rev. Infect. Dis.* 8(5) 693–704 (1986).

Johnston et al., "Isolation of the Yeast Regulatory Gene Ga14 and Analysis of its Dosage Effects on the Galactose/melibiose Regulon," *Proc. Natl. Acad. Sci. USA* 79:6971–6975 (1982).

Joyner et al., "Production of a Mutation in Mouse En–2 Gene by Homologous Recombination in Embryonic Stem Cells," *Nature* 338, 153–156 (1989).

Kappes et al., "Human Class II Major Histocompatibility Complex Genes and Proteins" *Ann. Rev. Biochem.* 57, 991–1028 (1988).

Kasprzak et al., "Location of a Contact Site Between Acting and Myosin in the Three–Dimensional Structure of the Acto–S1 Complex," *Biochemistry* 28, 9230–9238 (1989).

Kendall et al., "Plasmid Transfer in *Streptomyces lividans:* Identification of a kil–kor System Associated with the Transfer Region of PIJ101," *J. of Bacteriology* 169(9) 4177–4183 (1987).

Killen et al., "Specific Killing of Lymphocytes that Cause Experimental Autoimmune Myasthenia Gravis by Ricin Toxin–Acetylcholine Receptor Conjugates," *J. of Immunol.* 133(5) 2549–2553 (1984).

Kozak, "Compilation and Analysis of Sequences Upstream from the Translational Start Site in Eukaryotic mRNAs," *Nucleic Acids Research* 12(2) 857–872 (1984).

Kozak et al., "An Analysis of 5'–noncoding Sequences from 699 Vertebrate Messenger RNAs," *Nucl. Acids Res.* 15(20) 8125–8148 (1987).

Krueger et al., "A Human Transmembrane Protein–tyrosine–phosphatase, Ptpδ, Is Expressed in Brain and Has an N–terminal Receptor Domain Homologous to Carbonic Anhydrases," *Proc. Natl. Acad. Sci. USA* 89, 7417–7421 (1992).

Kunkel, "Rapid and Efficient Site–specific Mutagenesis Without Phenotypic Selection," *Proc. Natl. Acad. Sci. USA* 82, 488–492 (1985).

Kyte and Doolittle, "A Simple Method for Displaying the Hydropathic Character of a Protein," *J. Mol. Biol.* 157:105–132 (1982).

Lammers et al., "Differential Activities of Protein Tyrosine Phosphatases in Intact Cells," *J. Biol Chem.* 268, 22456–22462 (1993).

Lechner et al., "ERK6, A Mitogen–activated Protein Kinase Involved in C2C12 Myoblast Differentiation" *Proc. Natl. Acad. Sci. USA* 93:4355–4359 (1996).

Lutz et al., "The Distribution of Two hnRNP–Associated Proteins Defined by a Monoclonal Antibody Is Altered in Heat–Shocked HeLa Cells" *Exp. Cell Res.* 175, 109–124 (1988).

Malissen et al., "Nucleotide Sequence of a Light Chain Gene of the Mouse I–A Subregion: Aβ$^d$" *Science* 221:750–754 (1983).

Matthews et al., "Characterization of Hematopoietic Intracellular Protein Tyrosine Phosphatases: Description of a Phosphatase containing and SH2 Domain and Another Enriched in Proline–, Glutamic Acid–, Serine–, and Threonine–Rich Sequences" *Mol. Cell. Biol.* 12(5) 2396–2405 (1992).

Matviw et al., "Identification of a Human cDNA Encoding a Protein That Is Structurally and Functionally Related to the Yeast Adenylyl Cyclase–Associated CAP Proteins" *Mol. Cell Biol.* 12(11) 5033–5040 (1992).

Mauro et al., "Homophilic and Heterophilic Binding Activities of Nr–CAM, a Nervous System Cell Adhesion Molecule" *J. Cell Biol.* 119, 191–202 (1992).

McKnight, "Functional Relationships between Transcriptional Control Signals of the Thymidine Kinase Gene of Herpes Simplex Virus," *Cell* 31, 355–365 (1982).

Miller et al., "An Insect Baculovirus Host–Vector System for High–Level Expression of Foreign Genes," *Genetic Engineering: Principles and Methods,* edited by Setlow et al., Plenum Press, 8:277–298 (1986).

Miller, "Human gene therapy comes of age," *Nature* 357, 455–460(1992).

Mizuno et al., "Developmental Regulation of Gene Expression for the MPTPδ Isoforms in the Central Nervous System and the Immune System" *FEBS* 355, 223–228 (1994).

Nayler et al. "SAF–B Protein Couples Transcription and Pre–Mrna Splicing to SAR/MAR Elements" *Nucl. Acid. Res.* 26(15) 3542–3549 (1998).

Okayama et al., "A cDNA Cloning Vector That Permits Expression of cDNA Inserts in Mammalian Cells," *Mol. and Cell Biol.* 3, 280–289 (1983).

Puissant et al., "An Improvement of sthe Single–Step Method of RNA Isolation by Acid Guanidinium Thiocyanate–Phenol–Chloroform Extraction" *Biotechniques* 8(2) 148–149 (1990).

Pursel et al., "Genetic Engineering of Livestock," *Science* 244, 1281–1288 (1989).

Rogers et al., "Amino Acid Sequences Conmmon to Rapidly Degraded Proteins: The Pest Hypothesis" *Science* 234:364–368 (1986).

Rubin, "*Drosophila melanogaster* as an Experimental Organism," *Science,* 240, 1453–1459 (1988).

Saito et al., "Molecular Characterization of Protein Tyrosine Phosphatases," *Cell Growth & Differentiation* 2, 59–65 (1991).

Sanger et al., "DNA Sequencing with Chain–terminating Inhibitors," *Proc. Natl. Acad. Sci. USA* 74, 5463–5467 (1977).

Silver et al., "Amino Terminus of the Yeast Gal4 Gene Product Is Sufficient for Nuclear Localization," *Proc. Natl. Acad. Sci. USA* 81, 5951–5955 (1984).

Simons et al., "Gene Transfer Into Sheep" *Bio/Technology* 6:179–182 (1988).

Smith et al., "Single–step Purification of Polypeptides Expressed in *Escherichia Coli* as Fusions with Glutathione S–transferase" *Gene,* 67:31–40 (1988).

St. Groth et al., "Production of Monoclonal Antibodies: Strategy and Tactics," *J. Immunol. Methods* 35:1–21 (1980).

Sternberger et al. "The Unlabeled Antibody Enzyme Method of Immunohistochemistry" *J. Histochem. Cytochem.* 18(5) 315–333 (1970).

Stuckey et al., "Crystal Structure of Yersinia Protein Tyrosine Phosphatase at 2.5 Å and the Complex with Tungstate" *Nature* 370:571–575 (1994).

Su et al., "The Crystal Structure of a Low–Molecular–Weight Phosphotyroisine Protein Phosphatase" *Nature* 370, 575–578 (1994).

Takagi et al., "The A5 Antigen, a Candidate for the Neuronal Recognition Molioculem Has Homologies to Complement Components and Coagulation Factors" *Neuron.* 7:295–307 (1991).

Takekawa et al., "Cloning and characterization of a human cDNA encoding a novel putative cytoplasmic protein–tyrosine–phosphatase," *Biochem. Biophys. Res. Commun.* 189:1223–1230 (1992).

Thomas et al., "Structural Modification of Acidic Fibroblast Growth Factor Alter Activity, Stability, and Heparin Dependence" *Ann. NY Acad. Sci.* 8–17 (1991).

Tijssen, *Practice and Theory of Enzyme Immunoassays: Laboratory Techniques in Biochemistry and Molecular Biology,* vol. 15, Elsevier Science Publishers, Amsterdam, The Netherlands (Table of Contents Only). (1985).

Ullrich et al., "Rat Insulin Genes: Construction of Plasmids Containing the Coding Sequences" *Science* 196:1313–1319 (1977).

Ulmanen et al., "Transcription and Translation of Foreign Genes in *Bacillus subtilis* by the Aid of a Secretion Vector," *J. of Bacteriology* 162, 176–182 (1985).

Vojtek et al., "Mammalian Ras Interacts Directly with the Serine/Threonine Kinase Raf," *Cell* 74:205–214 (1993).

Von Heijne, "A New Method for Predicting Signal Sequence Cleavage Sites" *Nucleic Acids Res.* 14(11) 4683–4691 (1986).

Ward et al., "Construction and Characterisation of a Series of Multi–copy Promoter–probe Plasmid Vectors for Streptomyces Using the Aminoglycoside Phosphotransferase Gene from Tn5 as Indicator," *Mol. Gen. Genet.* 203, 468–478 (1986).

Yang et al., "Cloning and Expression of PTP–PEST," *J. Biol. Chem.* 268, 6622–6628 (1993).

Yang et al., "In Vivo and In Vitro Gene Transfer to Mammalian Somatic Cells by Particle Bombardment," *Proc. Natl. Acad. Sci. USA* 87, 9568–9572 (1990).

Yun et al., "The Doa Locus Encodes a Member of a New Protein Kinase Family and is Essential for Eye and Embryonic Development in Drosophila Melanogaster" *Genes Dev.* 8, 1160–1173 (1994).

Zahler et al., "SR Proteins: A Conserved Family of Pre–mRNA Splicing Factors" *Genes Dev.* 6, 837–847 (1992).

Zelicof et al., "Molecular Cloning and Characterization of a Rat Homolog of CAP, The Adenylyl Cyclase–Associated Protein From *Saccharomyces Cervisiae*" *J. of Biol. Chem.* 268(18) 13448–13453 (1993).

Zhang, et al., "Dissecting the Catalytic Mechanism of Protein Tyrosin Phosphatases" *Proc. Natl. Acad. Sci. USA* 91:1624–1627 (1994).

Cheng, et I., *EMBI Accession No. U49853*, "Mus Musculus Protein Tyrosine Phsophatase, mRNA, Complete cds." Mar. 27, 1996.

Nayler et al., "Characterization and comparison of four serine– and arginine–rich (SR) protein kinases," *Biochem. J.* 326:693–700 (1997).

Tomic, S. et al.: "Association of SH2 domain Protein Tyrosine Phosphatases with the Epidermal Growth Factor receptor in human tumor cells" Journal of Biological Chemistry. (Microfilms), vol. 270, No. 36, Sep. 8, 1995, MD US, pp. 21277–21284, XP002053898 see the whole document.

Aoki, N. et al.: "The novel protein–tyrosine phosphatase PTP20 is a positive regulator of PC12 cell neuronal differentiation" Journal of Biological Chemistry. (Microfilms), vol. 271, No. 46, Nov. 15, 1996, MD US, pp. 29422–29426, XP002053901 see the whole document.

Cheng J. et al: "A Novel Protein Tyrosine Phosphatase Expressed in L0CD34HISCAHI Hematopoietic Progenitor Cells" Blood, vol. 88, No. 4, Aug. 15, 1996, pp. 1156–1167, XP002034266 see the whole document.

Kim Y. W. et. al: "Characterization of the Pest Family Protein Tyrosine Phosphatase BDP1" Oncogene, vol. 13, No. 10, Nov. 21, 1996, pp. 2275–2279, XP002034272 see the whole document.

Wang, H. et al.: "Characterization of PCP–2, a novel receptor protein tyrosine phosphatase of the MAM domain family" Oncogene, vol. 12, No. 12, Jun. 20, 1996, pp. 2555–2562, XP002064033 see the whole document.

Winfield, S. L. et al.: "Identification of three additional genes contiguous to the glucocerebrosidase locus on chromosome 1Q21: implications for Gaucher disease" *Genome Research.*, vol. 7, No. 10, 1997, Ing Harbor Laboratory Press US, pp. 1020–1026, XP002064037 see the whole document.

Hanes, J.J. et al.: "Characterization by cDNA cloning of two new human protein kinases: evidence by sequence comparison for a new family of mammalian protein kinases" Journal of Biological Chemistry (Microfilms), vol. 244, No. 5, 1994, MD US, pp. 665–672, XP002054038 see the whole document.

Becker, W. et al.: "cDNA cloning and characterization of rat C1k3, a Lammer Kinase predominantly expressed in testis" Biochim. Biophy. Acta, vol. 1312, No. 1, Jun. 5, 1996, Orlando, FL US, pp. 63–67, XP002064040 see the whole document.

Johnson, K.W. & Smith, K.A.: "Molecular cloning of a novel human cdc2/CDC28–like protein" Journal of Biological Chemistry (Microfilms), vol. 266, No. 6, Feb. 25, 1991, MD US, pp. 3402–3407, XP002064041 see the whole document.

Wu et al., "Molecular Cloning of a Transcriptional Repressor Protein (SIRP–1) Which Binds to the Intestine–Specific Promoter Reigon of the Sucrase–Isomaltase Gene," *Gastroenterology* 104(4, part 2):A290 abstract (1993).

Abe et al., "Molecular Characterization of a Novel Metabotropic Glutamate Receptor mGluR5 Coupled to Inositol Phosphate/$Ca^{2+}$ Signal Transduction", *J. Biol. Chem.*, 19:13361–13368 (1992).

Anderson et al., "Binding of SH2 Domains of Phospholipase C$\gamma$1, GAP, and Src to Activated Growth Factor Receptors", *Science*, 250:979–982 (1990).

Carpenter et al., "Epidermal Growth Factor" *J. Biol. Chem.*, 265:7709–7712 (1990).

Chen et al. "High–Efficiency Transformation of Mammalian Cells by Plasmid DNA" *Mol. Cell. Biol.*, 7:2745–2752 (1987).

Fendly et al., "Characterization of Murine Monoclonal Antibodies Reactive to Either the Human Epidermal Growth Factor Receptor or HER2/neu Gene Product", *Cancer Res.*, 50:1550–1558 (1990).

Fry et al., "New Insights into Protein–Tyrosine Kinase Receptor Signaling Complexes" *Protein Science*, 2:1785–1797 (1993).

Jansen et al., "Immunotoxins: Hybrid Molecules Combining High Specificity and Potent Cytotoxicity" *Immunological Rev.*, 62:185–216 (1982).

Kazlauskas et al., "Phosphorylation of the PDGF Receptor $\beta$ Subunit Creates a Tight Binding Site for Phosphatidylinositol 3 Kinase", *EMBO J.*, 9:3279–3286 (1990).

Kazlauskas et al., "Binding of GAP to Activated PDGF Receptors", *Science*, 247:1578–1581 (1990).

Kharitonenkov et al., "A Family of Proteins that Inhibit Signalling Through Tyrosine Kinase Receptors" *Nature*, 386:181–186 (1997).

Killen et al., "Specific Killing of Lymphocytes that Cause Experimental Autoimmune Myasthenia Gravis by Ricin Toxin–Acetylcholine Receptor Conjugates" *J. Immunol.*, 133:1335–2549 (1984).

Kumjian et al., "Platelet–Derived Growth Factor (PDGF) Binding Promotes Physical Association of PDGF Receptor with Phospholipase C", *Proc. Natl. Acad. Sci. USA* 86:8232–8239 (1989).

Margolis et al., "Tyrosine Kinase Activity is Essential for the Association of Phospholipase C–$\gamma$ with the Epidermal Growth Factor Receptor", *Mol. Cell. Biol.*, 10:435–441 (1990).

Mayer et al., "A Novel Viral Oncogene with Structural Similarity to Phospholipase C", *Nature*, 332:272–275 (1988).

Millauer et al., "Glioblastoma Growth Inhibited in vivo by a Dominant Negative Flk–1 Mutant", *Nature*, 367:576–579(1994).

Miller et al., "Improved Retroviral Vectors for Gene Transfer and Expression", *Biotechniques*, 7:980–988 (1989).

Morrison et al., "Direct Activation of the Serine/Threonine Kinase Activity of Raf–1 Through Tyrosine Phosphorylation by the PDGF β–Receptor", *Cell*, 58:649–657 (1989).

Nelson et al., "Nonisotopic DNA Probe Techniques", *Academic Press, San Diego* 275–310 (Kricka, ed., 1992).

Ohnishi et al., "Activation of Protein–Tyrosine Phosphatase SH–PTP2 by a Tyrosine–Based Activation Motif of a Novel Brain Molecule", *J. Biol. Chem.*, 271:25569–25574 (1996).

Pawson, "Non–Catalytic Domains of Cytoplasmic Protein–Tyrosine Kinases: Regulatory Elements in Signal Transduction", *Oncogene*, 3:491–495 (1988).

Pear et al., "Production of High–Titer Helper–Free Retroviruses by Transient Transfection", *Proc. Natl. Acad. Sci.*, 90:8392–8396 (1993).

Redemann et al., "Anti–Oncogenic Activity of Signalling–Defective Epidermal Growth Factor Receptor Mutants", *Mol. Cell. Biol.*, 12:491–498 (1992).

Schlessinger et al., "Growth Factor Signaling by Receptor Tyrosine Kinases", *Neuron*, 9:383–391 (1992).

Stein–Gerlach et al., "Protein–Tyrosine Phosphatase 1D Modulates its Own State of Tyrosine Phosphorylation", *J. Biol. Chem.*, 270:24635–24637 (1995).

Ullrich et al., "Signal Transduction by Receptors with Tyrosine Kinase Activity", *Cell*, 61:203–212 (1990).

Vogel et al., "Activation of a Phosphotyrosine Phosphatase by Tyrosine Phosphorylation", *Science*, 259:1611–1614 (1994).

Yamauchi et al., "Epidermal Growth Factor–Induced Association of the SHPTP2 Protein Tyrosine Phosphatase with a 115–kDa Phosphotyrosine Protein", *J. Biol. Chem.*, 270:14871–14874 (1995).

Yamauchi , et al., "Identification of the Major SHPTP2–Binding Protein that is Tyrosine–Phosphorylated in Response to Insulin", *J. Biol. Chem.* 270:17716–17722 (1995).

\* cited by examiner

FIG. 1

```
             *****▶
SIRP4  MEPAGPAPGRLGPLLCLLLAASCAWSGVAGEEELQVIQPDKSVSVAAGESAILHCTVT   58
SIRP1  MPVPASWPHLPSPFLLMTLLLGRLTGVAGEDELQVIQPEKSVSVAAGESATLRCAMT   57

4   SLIPVGPIQWFRGAGPARELIYNQKEGHFPRVTTVSESTKRENMDFSISISNITPADA  116
   1   SLIPVGPIMWFRGAGAGRELIYNQKEGHFPRVTTVSELTKRNNLNFSISISNITPADA  115

◀*****
   4   GTYYCVKFRKGSPDT-EFKSGAGTELSVRAKPSAPVVSGPAARATPQHTVSFTCESHG  173
   1   GTYYCVKFRKGSPDDVEFKSGAGTELSVRAKPSAPVVSGPAVRATPEHTVSFTCESHG  173

4   FSPRDITLKWFKNGNELSDFQTNVDRVGESVSYSIHSTAKVVLTREDVHSQVICEVAH  231
   1   FSPRDITLKWFKNGNELSDFQTNVDRAGDSVSYSIHSTARVVLTRGDVHSQVICEMAH  231

4   VTLQGDPLRGTANLSETIRVPPTLEVTQQEVRAENQMNVTCQVRKFYPQRLQLTWLEN  289
   1   ITLQGDPLRGTANLSEAIRVPPTLEVTQQEMRAENQANVTCQVSNFYBRGLQLTWLEN  289

4   GNVSRTETASTVTENKDGTYNWMSWLLVNVSAHRDDVKLTCQVEHDGQPAVSKSHDLK  347
   1   GNVSRTETASTLIENKDGTYNWMSWLLVNTCAHRDDVWLTCQVEHDGQQAVSKSYALE  347

4   VSAHPKEQGSNTAAENTGSNERNIYIVVGVVCTLLVALLMAALYLVRIRQKKAQGSTS  405
   1   ISAHQKEHGSDITHEPALAPTAPLLVALLLGPKLLLVVGVSAIYICWKQKA         398

4   STRLHEPEKNAREITQDTNDITYADLNLPKGKKPAPQAAEPNNHTEYASIQTSPQPAS  463

4   EDTLTYADLDMVHLNRTPKQPAPKPEPSFSEYASVQVPRK                    503
```

FIG. 2

```
Ex1         DELQVIQPEKSVSVAAGESATLRCAMTSLIPVGPIMWFRGAGAGRELIYNQKEGHF
SIRP4    33 EELQVIQPDKSVSVAAGESAILHCTVTSLIPVGPIQWFRGAGPARELIYNQKEGHF
SIRP1    32 DELQVIQPEKSVSVAAGESATLRCAMTSLIPVGPIMWFRGAGAGRELIYNQKEGHF
Ex2         DELQVIQPEKSVSVAAGESATLRCAMTSLIPVGPIMWFRGAGAGRELIYNQKEGHF
Ex3         EELQVIQPEKSVLVAAGETATLRCTATSLIPVGPIMWFRGAGAGRELIYNQKEGHF
Ex4         EELQVIQPDKSVSVAPGESAILHCTVTSLIPVGPIQWFRGAGPARELIYNQKEGHF
Ex5         DELQVIQPDKSVSVAAGESATLRCAMTSLIPVGPIMWFRGAGAGRELISNQKEGHF
Ex6         DELQVIQPEKSVSVAPGESATLRCAMTSLIPVGPIMWFRGAGAGRELISNQKEGHF
Ex7         EELQVIQPDKSVSVAPGESAILHCTVTSLIPVGPIQWFRGAGPARELIYNQKEGHF
Ex8         EELQVIQPDKSVSVAPGESAILHCTVTSLIPVGPIQWFRGAGPARELIYNQKEGHF
Ex9         DELQVIQSEKSVSVAAGESAALHCAMTSLIPVGPIMWFRGAGAGRELIYNQKEGHF
Ex10        DELQVIQPEKSVSVAAGESATLRCAMTSLIPVGPIMWFRGAGAGRELIYNQKEGHF
Ex11        DELQVIQPEAFVSVAAGEMATLNCTVTSLLPVGPIQWFRGACPGDKLIYSPKRCHS
Ex12        EELQMIQPEKLLLVTVGKTATLHCTVTSLLPVGPVLWFRGVGPGRELIYNQKEGHF
Ex13        EELQVIQPEKSVSVAAGESAALQCTVTSLNPVGPIQRFRGAGPGRKLIYHQKEGHF

Ex1         PRVTTVSELTKRNNLDFSISISNITPADAGTYYCVKFREGSPDDVEFKSGA
SIRP4    89 PRVTTVSESTKRENMDFSISISNITPADAGTYYCVKFRKGSPD-TEFKSGA  139
SIRP1    88 PRVTTVSELTKRNNLNFSISISNITPADAGTYYCVKFRKGSPDDVEFKSGA  139
Ex2         PRVTTVSELTKRNNLDFSISISNITPADAGTYYCVKFRKGSPDDVEFKSGA
Ex3         PRVTTVSDLTKRNNMDFSIRIGNITPADAGTYYCVKFRKGSPDDVEFKSGA
Ex4         PRVTTVSESTKRENMNFSISISNITPADAGTYYCVKFRKGSPDDVEFKSGA
Ex5         PRVTTVSESTKRENMDFSISISNITPADAGTYYCVKFRKGSPDDVEFKSGA
Ex6         PRVTTVSELTKRNNLDFSISISNITPADAGTYYCVKFRKGSPDDVEFKSGA
Ex7         PRVTTVSDLTKRNNLDFSISISNITPADAGTYYCVKFRKGSPD-VEFKSGA
Ex8         PRVTTVSESTKRENLDFSISISNITPADAGTYYCVKFRKGSPD-VEFKSGA
Ex9         PRVTTVSELTKRNNLDFSISISNITPADAGTYYCVKFRKGSPDDVEFKSGA
Ex10        PRVTTVSELTKRNNLDFSIRISNITPADAGTYYCVKFRKGSPDDVEFKSGA
Ex11        PRVTTISDQRKRNSTDYSIRISSITLEDAGTYYCMKLRRAIPANVEIKSGT
Ex12        PRVTRVSDLTKRNNMDFSIRISSITPAVVGTYYCVKFRKGSPENVEFKSGP
Ex13        PRVTTVSDLTKRTNMDFSICISNITPADAGTYYCVKFQKGSPD-VELKSGA
```

FIG. 3

```
  1  MEPAGPAPGRLGP--LLCLLLAASCAWSGVAGEEELQVIQPDKSVSVAAGESAILHCTVT  SIRP4_h
  1  MEPAGA-PQRLGP-LLLCLLLSASCFCTGVTGKE-LKVTQPEKSVSVAAGDSTVLNCTLT  SIRPa1_m
  1  MPVPASWHHLPSDFLLMTLLLG---RLTGVAGEDELQVIQPEKSVSVAAGESATLRCANT  SIRP1_h
  1  MLLLDAWTHIPHCVLLLILLLGLK-----GAAMRELKVIQPVKSFPVGAGGSATLNCTVT  SIRPb1_m

59  SLIPVGPIQWFRGAGPARELIYNQKEGHFPRVTTVSESTKRENMDFSISISNITPADAGT  SIRP4_h
 59  SLIPVGPIRWYRGVGKAGCLIYSFTGEHFPRVTNVSDATKRNNMDFSIRISNVTPEDAGT  SIRPa1_m
 59  SLIPVGPDMWFRGAGAGRELIYNQKEGHFPRVTTVSELTKRNNLNFSISISNITPADAGT  SIRP1_h
 56  SLLPVGPMRWYRGIGQSRLLIYSFTGEGFPRIINTSDTKRNNMDFSIRISNVTPADSGT  SIRPb1_m

119  YYCVKFRKGSPD-T-EFKSGAGTELSVRAKPSAPVVSGPAARATPQHTVSFTCESHGFSP  SIRP4_h
118  YYCVKFQKGPSEPDTEICSGGGTEVYVLAKPSEPE-DPRRQGHTDQKVNFTCKSHGFSP  SIRPa1_m
118  YYCVKFRKGSPD-DVEPKSGAGTELSVRAKPSAPVVSGPAVRATPEHTVSFTCESHGFSP  SIRP1_h
116  YYCVKFQRGPSDPYTEIQSGGGTELSVLAKPSSEMVSGPAARAVPQQTVTFTCRSHGFPP  SIRPb1_m

177  RDITLKWFKNGNELSDFQTNVDPVGESVSYSIHSTAKVVLTREDVHSQVICEVAHVTLQG  SIRP4_h
177  RNITLKWFKDGQELHPLETTVNPSGKNVSYNIGSTVRVVLNSMDVHSKVICEVAHITLDR  SIRPa1_m
177  RDITLKWFKNGNELSDFQTNVDPAGDSVSYSIHSTARVVLTRGDVHSQVICEMAHITLQG  SIRP1_h
176  RNLTLKWFKNGDEISHLETSVEEETSVSYRVSSTVQVVLEPRDVRSQIICEVDHVTLDR  SIRPb1_m

237  DPLRGTANLSETIRVPPTLEVTQQPVRAENQVNVTCQVRKFYPQRLQLTWLENGNVSRTE  SIRP4_h
237  SPLRGIANLSNFIRVSPTVKVTQQSPTSHNQVNLTCRDERFYPEDLQLIWLENGNVSRND  SIRPa1_m
237  DPLRGTANLSEAIRVPPTLEVTQQPMRAENQANVTCQVSNPYPRGLQLTWLENGNVSRTE  SIRP1_h
236  APLRGIAHISEFLQVPPTLEIRQQPTHVWNVINVTCQIQKFYPPSFQLTWLENGNISRRE  SIRPb1_m

297  TASTVTENKDGTYNWMSWLLVNVSAHRDDVKLTCQVEHDGQPAVSKSHDLKVSAHPKEQG  SIRP4_h
297  TPKNLTKMTDGTYNYTSLFLVNSSAHREDVVFTCQVKHDQQPAITRNHTVLQLAHSSDQG  SIRPa1_m
297  TASTLIENKDGTYNWHSWLLVNTCAHRDDVVLTCQVEHDGQQAVSKSYAEEISAHQKEHG  SIRP1_h
296  VPFTLTVNKDGTYNWISCLLVNIGALEENMVVTCQVEHDGQAEVIETHTVVVTEHQRVKG  SIRPb1_m

357  S-NTAAENTGSNERNIYIVVGVVCTLLVALLMAALYLVRIRQKKAQGSTSSTRLHEPEKN  SIRP4_h
357  SHQTPPGNNATHNWHVFLGVGVAGALLVMLMAALYLLRIKQKKAKGSTSSTRLHEPEKN  SIRPa1_m
357  S-DITHEPA---------LAPTAPLLVALLLGPKLLLVVGVSAIYICWKQKA          SIRP1_h
356  --------TATKSGEVF-----TPPLCLNVNWALFFHYKVTFLIIVALS             SIRPb1_m

416  AREITQ---------DTNDITYADLNLPKGKKPAPQAAE-PNNHTEYASIQTSPQPASED  SIRP4_h
417  AREITQVQSLIQDTNDINDITYADLNLPKRRKPAPGSLEFLNNHTEYASIETGKVPRPED  SIRPa1_m
398                                                                 SIRP1_h
391                                                                 SIRPb1_m

466  TLTYADLDMVHLNRTPKQPAPKPEPSFSEYASVQVPRK  SIRP4_h
477  TLTYADLDMVHLSEAQ--PAPKPEPSFSEYASVQVQRK  SIRPa1_m
398                                          SIRP1_h
391                                          SIRPb1_m
```

SIRP PROTEINS AND USES THEREOF

This application claims priority to U.S. provisional application No. 60/030,964 filed Nov. 15, 1996.

BACKGROUND OF THE INVENTION

Signal transduction is a fundamental mechanism whereby external stimuli are relayed to the interior of cells. A key aspect of signal transduction involves the reversible phosphorylation of tyrosine residues on proteins. The phosphorylation state of tyrosine residues on a protein is modified through the reciprocal actions of tyrosine kinases (TKs) and tyrosine phosphatases (TPs).

For example, a variety of polypeptide growth factors and hormones mediate their cellular effects by interacting with cell surface receptors and soluble or cytoplasmic polypeptide containing molecules having tyrosine kinase enzymatic activity (for review, see Williams, et al. *Cell* 61:203–212 (1990); Carpenter, et al. *J. Biol. Chem.* 265:7709–7712 (1990)). The interaction of these ligands with their receptors induces a series of events which include receptor dimerization and stimulation of protein tyrosine kinase activity. Tyrosine autophosphorylation on multiple sites creates specific binding sites for target proteins, which bind to the activated receptor with their SH2 domains (for review, see Schlessinger and Ullrich, *Neuron* 9:383–391, (1992)).

SH2 (src homology 2) domains are conserved sequences of about 100 amino acids found in cytoplasmic non-receptor tyrosine kinases such as pp60src, PLC-γ, GAP and v-crk (Mayer, et al., *Nature* 332:272–275 (1988); Pawson, *Oncogene* 3:491–495 (1988)). While having distinct catalytic domains, all these molecules share conserved SH2 and SH3 (src homology 3) domains and the ability to associate with receptors with tyrosine kinase activity (Anderson, et al. *Science* 250:979–982 (1990)).

Tyrosine kinase activation and receptor autophosphorylation are prerequisites for the association between growth factor receptors and SH2 domain-containing proteins (Margolis, et al., *Mol. Cell. Biol.* 10:435–441 (1990); Kumjian et al., *Proc. Natl. Acad. Sci. USA* 86:8232–8239 (1989); Kazlauskas, et al., *Science* 247:1578–1581 (1990)). In particular, the carboxy-terminal (C-terminal) fragment of the epidermal growth factor receptor (EGFR), which contains all the known autophosphorylation sites, binds specifically to the SH2 domains of GAP and PLC-γ (see below). Hence, a major site of association exists between the SH2 domain of these substrate proteins and the tyrosine phosphorylated C-terminal tail of the EGFR.

Target proteins which bind to activated receptors have been identified by analysis of proteins that co-immunoprecipitate with growth factor receptors, or that bind to receptors attached to immobilized matrices (Morrison, et al., *Cell* 58:649–657 (1989); Kazlauskas, et al., *EMBO J.* 9:3279–3286 (1990)).

Ohnishi et al. *J. Biol. Chem.* 271:25569–25574 (1996), not admitted to be prior art, described that a brain specific immunoglobulin-like molecule with tyrosine-based activation motifs, BIT, is associated with protein-tyrosine phosphatase SH-PTP2, whereby two SH2 domains of SH-PTP2 simultaneously interact with two phosphotyrosines of BIT-TAM.

Phosphotyrosine phosphatases (PTPs) are involved with negative or positive regulation of growth factor-specific cell responses such as mitosis, differentiation, migration, survival, transformation or death. For example, SHP-2 is a phosphotyrosine phosphatase which contains a SH2 domain. SHP-2 is a positive signal transducer for a number of receptor tyrosine kinases (RTKS) and cytokine receptors.

SUMMARY OF THE INVENTION

Within the scope of this invention, applicant has identified a novel mammalian protein family of at least fifteen members designated SIgnal Regulatory Proteins (SIRPs. In particular, Applicant has cloned and sequenced the coding sequences of 4 members of SIRPs, SIRP1 and SIRP4 from human, and SIRPα1 and SIRPβ1 from mouse. In this regard, the present invention relates to SIRP polypeptides, nucleic acids encoding such polypeptides, cells, tissues and animals containing such polypeptides or nucleic acids, antibodies to such polypeptides or nucleic acids, assays utilizing such polypeptides or nucleic acids, and methods relating to all of the foregoing.

SIRP family proteins play a general role in the regulation of signals that define diverse physiological and pathological processes. Thus, the present invention provides several agents and methods useful for diagnosing, treating, and preventing various diseases or conditions associated with abnormalities in these pathways as well as assay systems useful for screening for therapeutically effective agents.

In particular, SIRP polypeptides are involved in various signal transduction pathways such as the negative regulation of signals generated by receptor tyrosine kinases, including, but not limited to, receptors for EGF, insulin and platelet derived growth factor (PDGF). For example, acting like a tumor suppressor, SIRP4 exerts negative regulatory effects on growth factor and hormone induced cellular responses such as DNA synthesis. Oncogenesis may be associated with mutant SIRPs or not enough SIRPs. Restoring SIRPs to their normal levels such as by gene therapy could restore the cells to a normal growth pattern. Insulin receptor activity is also regulated by SIRPs. Overexpression of SIRPs may be involved in type II diabetes where sufficient insulin is present but insulin signaling is deficient. A compound that inhibits the negative regulation of insulin signaling by SIRPS, such as by interfering with the interaction between SIRP and SHP-2 may lead to enhanced insulin signaling.

All SIRP proteins have a receptor-like, or Immunoglubulin (Ig) like extracellular domain and a transmembrane domain. There are two subtypes of SIRPs distinguished by the presence or absence of a cytoplasmic SHP-2 binding domain. For example, SIRP4 has a cytoplasmic domain while SIRP1 doesn't. The cytoplasmic domain of SIRP4 contains two SHP-2 binding regions each having two tyrosine residues.

The growth inhibitory effect of SIRP4 depends on phosphorylation of tyrosines and is related to reduced MAP kinase activation. SIRP4 becomes a substrate of activated receptor tyrosine kinases (RTKs) upon EGF, insulin or PDGF stimulation. In its tyrosine phosphorylated form, SIRP4 binds a phosphotyrosine phosphatase, SHP-2, via SH2 interactions. Once SIRP4 binds SHP-2, it activates the catalytic activity of SHP-2 and becomes a substrate of SHP-2. This direct activation of SHP-2 could induce activation of Src or other Src family kinases. The above described interaction allows SIRP4 to participate in major signal transduction pathways involving SHP-2.

SHP-2 has two SH2 domains and is required for signaling downstream of a variety of RTKs. SHP-2 has been reported to bind directly to RTKs such as PDGF receptor, EGF receptor, and cKit in response to stimulation by their ligands. Insulin receptor substrate 1 (IRS-1) also associates with SHP-2 in response to insulin.

SIRP4 also binds SHP-1 and Grb2, both of which contain a SH-2 domain. Grb2 is an adapter molecule and one of its functions is to link growth factor receptors to downstream effector proteins. Grb2 is known to bind tyrosine-phosphorylated SHP-2 in response to PDGF stimulation.

The full length nucleic acid sequences encoding hSIRP1, hSIRP4, mSIRPα1 and mSIRPβ1 proteins are set forth respectively in SEQ ID NO:1, SEQ ID NO:2, SEQ ID NO:3, and SEQ ID NO:4. The coding regions are nt 41–1237 of SEQ ID NO:1, nt 13–1524 of SEQ ID NO:2, nt 59–1597 of SEQ ID NO:3, and nt 86–1261 of SEQ ID NO:4.

The full length amino acid sequences of hSIRP1, hSIRP4, mSIRPα1 and mSIRPβ1 are set forth respectively in SEQ ID NO:5, SEQ ID NO:6, SEQ ID NO:7, and SEQ ID NO:8. The first two Ig-like domains of hSIRP1 is from aa 54–227; the third Ig-like domain is from aa 250–330; the extracellular domain next to the membrane is from aa 336–366; and the transmembrane domain is from aa 367–398. The first two Ig-like domains of hSIRP4 is from aa 1–227; the third Ig-like domain is from aa 250–336; the extracelluar domain next to the membrane, the transmembrane domain, and the cytoplasmic domain immediate next to the membrane are from aa 347–407; and the rest of the cytoplasmic domain is from aa 408–503.

Thus, in a first aspect the invention features an isolated, purified, enriched or recombinant nucleic acid encoding a SIRP polypeptide. Preferably such nucleic acid encodes a mammalian SIRP polypeptide, more preferably it encodes a human SIRP polypeptide.

By "isolated" in reference to nucleic acid is meant a polymer of 2 (preferably 21, more preferably 39, most preferably 75) or more nucleotides conjugated to each other, including DNA or RNA that is isolated from a natural source or that is synthesized. The isolated nucleic acid of the present invention is unique in the sense that it is not found in a pure or separated state in nature. Use of the term "isolated" indicates that a naturally occurring sequence has been removed from its normal cellular environment. Thus, the sequence may be in a cell-free solution or placed in a different cellular environment. The term does not imply that the sequence is the only nucleotide chain present, but does indicate that it is the predominate sequence present (at least 10–200 more than any other nucleotide sequence) and is essentially free (about 90–95% pure at least) of non-nucleotide material naturally associated with it. Therefore, the term does not encompass an isolated chromosome encoding one or more SIRP polypeptides.

By the use of the term "enriched" in reference to nucleic acid is meant that the specific DNA or RNA sequence constitutes a significantly higher fraction (2–5 fold) of the total DNA or RNA present in the cells or solution of interest than in normal or diseased cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that enriched does not imply that there are no other DNA or RNA sequences present, just that the relative amount of the sequence of interest has been significantly increased in a useful manner and preferably separate from a sequence library. The term significant here is used to indicate that the level of increase is useful to the person making such an increase, and generally means an increase relative to other nucleic acids of about at least 2 fold, more preferably at least 5 to 10 fold or even more. The term also does not imply that there is no DNA or RNA from other sources. The other source DNA may, for example, comprise DNA from a yeast or bacterial genome, or a cloning vector such as pUC19. This term distinguishes from naturally occurring events, such as viral infection, or tumor type growths, in which the level of one mRNA may be naturally increased relative to other species of mRNA. That is, the term is meant to cover only those situations in which a person has intervened to elevate the proportion of the desired nucleic acid.

It is also advantageous for some purposes that a nucleotide sequence be in purified form. The term "purified" in reference to nucleic acid does not require absolute purity (such as a homogeneous preparation); instead, it represents an indication that the sequence is relatively purer than in the natural environment (compared to the natural level this level should be at least 2–5 fold greater, e.g., in terms of mg/ml). Individual clones isolated from a cDNA library may be purified to electrophoretic homogeneity. The claimed DNA molecules obtained from these clones could be obtained directly from total DNA or from total RNA. The cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately $10^6$-fold purification of the native message. Thus, purification of at least one order of magnitude, preferably two or three orders, and more preferably four or five orders of magnitude is expressly contemplated.

By "SIRP polypeptide" is meant 9 or more contiguous amino acids set forth in the full length amino acid sequence of SEQ ID NO:5, SEQ ID NO:6, SEQ ID NO:7, or SEQ ID NO:8. The SIRP polypeptides can be encoded by full-length nucleic acid sequences or any portion of a full-length nucleic acid sequence, so long as a functional activity of the polypeptide is retained. Preferred functional activities include the ability to bind to a receptor tyrosine kinase or a SH-2 domain bearing protein such as SHP-2, SHP-1 or Grb-2. A non full-length SIRP polypeptide may be used to elicit an antibody against the polypeptide and the full-length polypeptide using techniques known to those skilled in the art. The present invention also encompasses deletion mutants lacking one or more isolated SIRP domains (e.g., Ig-like domain, transmembrane domain, SH2 binding domain, and tyrosine residues), and complementary sequences capable of hybridizing to full length SIRP protein under stringent hybridization conditions.

In preferred embodiments, isolated nucleic acid comprises, consists essentially of, or consists of a nucleic acid sequence set forth in the full length nucleic acid sequence SEQ ID NO:1, SEQ ID NO:2, SEQ ID NO:3, or SEQ ID NO:4 or at least 27, 30, 45, 60 or 90 contiguous nucleotides thereof and the SIRP polypeptide comprises, consists essentially of, or consists of at least 9, 10, 15, 20, 30, 50, 100, 200, or 300 contiguous amino acids of a SIRP polypeptide.

By "comprising" it is meant including, but not limited to, whatever follows the word "comprising". Thus, use of the term "comprising" indicates that the listed elements are required or mandatory, but that other elements are optional and may or may 0 o not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

Compositions and probes of the present invention may contain human nucleic acids encoding a SIRP polypeptide but are substantially free of nucleic acid not encoding SIRP polypeptide. The human nucleic acid encoding a SIRP polypeptide is at least 18 contiguous bases of the nucleotide sequence set forth in SEQ ID NO:1, SEQ ID NO:2, SEQ ID NO:3, or SEQ ID NO:4 and will selectively hybridize to human genomic DNA encoding a SIRP polypeptide, or is complementary to such a sequence. The nucleic acid may be isolated from a natural source by cDNA cloning or subtractive hybridization; the natural source may be blood, semen, and tissue of various organisms including eukaryotes, mammals, birds, fish, plants, gorillas, rhesus monkeys, chimpanzees and humans; and the nucleic acid may be synthesized by the triester method or by using an automated DNA synthesizer. In yet other preferred embodiments the nucleic acid is a conserved or unique region, for example those useful for the design of hybridization probes to facilitate identification and cloning of additional polypeptides, the design of PCR probes to facilitate cloning of additional polypeptides, and obtaining antibodies to polypeptide regions.

By "conserved nucleic acid regions", are meant regions present on two or more nucleic acids encoding a SIRP polypeptide, to which a particular nucleic acid sequence can hybridize to under lower stringency conditions. Examples of lower stringency conditions suitable for screening for nucleic acid encoding SIRP polypeptides are provided in Abe, et al. *J. Biol. Chem.*, 19:13361 (1992) (hereby incorporated by reference herein in its entirety, including any drawings). Preferably, conserved regions differ by no more than 7 out of 20 nucleotides.

By "unique nucleic acid region" is meant a sequence present in a full length nucleic acid coding for a SIRP polypeptide that is not present in a sequence coding for any other naturally occurring polypeptide. Such regions preferably comprise 12 or 20 contiguous nucleotides present in the full length nucleic acid encoding a SIRP polypeptide.

The invention also features a nucleic acid probe for the detection of a nucleic acid encoding a SIRP polypeptide in a sample. The nucleic acid probe contains nucleic acid that will hybridize to at least one sequence set forth in SEQ ID NO:1, SEQ ID NO:2, SEQ ID NO:3, or SEQ ID NO:4.

In preferred embodiments the nucleic acid probe hybridizes to nucleic acid encoding at least 12, 27, 30, 35, 40, 50, 100, 200, or 300 contiguous amino acids of the full-length sequence set forth in SEQ ID NO:5, SEQ ID NO:6, SEQ ID NO:7, or SEQ ID NO:8. Various low or high stringency hybridization conditions may be used depending upon the specificity and selectivity desired.

By "high stringency hybridization conditions" is meant those hybridizing conditions that (1) employ low ionic strength and high temperature for washing, for example, 0.015 M NaCl/0.0015 M sodium citrate/0.1 o SDS at 50° C.; (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.; or (3) employ 50% formamide, 5×SSC (0.75 M NaCl, 0.075 M Sodium pyrophosphate, 5×Denhardt's solution, sonicated salmon sperm DNA (50 g/ml), 0.1% SDS, and 10% dextran sulfate at 42° C., with washes at 42° C. in 0.2×SSC and 0.1% SDS. Under stringent hybridization conditions only highly complementary nucleic acid sequences hybridize. Preferably, such conditions prevent hybridization of nucleic acids having 1 or 2 mismatches out of 20 contiguous nucleotides.

Methods for using the probes include detecting the presence or amount of SIRP RNA in a sample by contacting the sample with a nucleic acid probe under conditions such that hybridization occurs and detecting the presence or amount of the probe bound to SIRP RNA. The nucleic acid duplex formed between the probe and a nucleic acid sequence coding for a SIRP polypeptide may be used in the identification of the sequence of the nucleic acid detected (for example see, Nelson et al., in *Nonisotopic DNA Probe Techniques*, p. 275 Academic Press, San Diego (Kricka, ed., 1992) hereby incorporated by reference herein in its entirety, including any drawings). Kits for performing such methods may be constructed to include a container means having disposed therein a nucleic acid probe.

The invention also features recombinant nucleic acid, preferably in a cell or an organism. The recombinant nucleic acid may contain a sequence (coding sequence or noncoding sequence) or a segment of sequence set forth in SEQ ID NO:1, SEQ ID NO:2, SEQ ID NO:3, or SEQ ID NO:4 and a vector or a promoter effective to initiate transcription in a host cell. The recombinant nucleic acid can alternatively contain a transcriptional initiation region functional in a cell, a sequence complimentary to an RNA sequence encoding a SIRP polypeptide and a transcriptional termination region functional in a cell.

In another aspect the invention features an isolated, enriched or purified SIRP polypeptide.

By "isolated" in reference to a polypeptide is meant a polymer of 2 (preferably 7, more preferably 13, most preferably 25) or more amino acids conjugated to each other, including polypeptides that are isolated from a natural source or that are synthesized. The isolated polypeptides of the present invention are unique in the sense that they are not found in a pure or separated state in nature. Use of the term "isolated" indicates that a naturally occurring sequence has been removed from its normal cellular environment. Thus, the sequence may be in a cell-free solution or placed in a different cellular environment. The term does not imply that the sequence is the only amino acid chain present, but that it is the predominate sequence present (at least 10–20% more than any other sequence) and is essentially free (about 90–95% pure at least) of non-amino acid material naturally associated with it.

By the use of the term "enriched" in reference to a polypeptide is meant that the specific amino acid sequence constitutes a significantly higher fraction (2–5 fold) of the total of amino acids present in the cells or solution of interest than in normal or diseased cells or in the cells from which the sequence was taken. This could be caused by a person by preferential reduction in the amount of other amino acids present, or by a preferential increase in the amount of the specific amino acid sequence of interest, or by a combination of the two. However, it should be noted that enriched does not imply that there are no other amino acid sequences present, just that the relative amount of the sequence of interest has been significantly increased. The term significant here is used to indicate that the level of increase is useful to the person making such an increase, and generally means an increase relative to other amino acids of about at least 2 fold, more preferably at least 5 to 10 fold or even more. The term also does not imply that there is no amino acid from other sources. The other source amino acid may, for example, comprise amino acid encoded by a yeast or bacterial genome, or a cloning vector such as pUC19. The term is meant to cover only those situations in which man has intervened to elevate the proportion of the desired amino acid.

It is also advantageous for some purposes that an amino acid sequence be in purified form. The term "purified" in reference to a polypeptide does not require absolute purity (such o0 as a homogeneous preparation); instead, it represents an indication.that the sequence is relatively purer than in the natural environment (compared to the natural level this level should be at least 2–5 fold greater, e.g., in terms of mg/ml). Purification of at least one order of magnitude, preferably two or three orders, and more preferably four or five orders of magnitude is expressly contemplated. The substance is preferably free of contamination at a functionally significant level, for example 90%, 95%, or 99% pure.

In preferred embodiments SIRP polypeptides contain at least 9, 10, 15, 20, or 30 contiguous amino acids of the full-length sequence set forth in SEQ ID NO:5, SEQ ID NO:6, SEQ ID NO:7, or SEQ ID NO:8.

In yet another aspect the invention features a purified antibody (e.a., a monoclonal or polyclonal antibody) having specific binding affinity to a SIRP polypeptide. The antibody contains a sequence of amino acids that is able to specifically bind to a SIRP polypeptide.

By "specific binding affinity" is meant that the antibody will bind to a hSIRP polypeptide at a certain detectable amount but will not bind other polypeptides to the same extent, under identical conditions. The present invention also encompasses antibodies that can distinguish hSIRP1 from hSIRP2 or hSIRP3 or can otherwise distinguish between the various SIRPs.

Antibodies having specific binding affinity to a SIRP polypeptide may be used in methods for detecting the presence and/or amount of a SIRP polypeptide is a sample by contacting the sample with the antibody under conditions such that an immunocomplex forms and detecting the presence and/or amount of the antibody conjugated to the SIRP polypeptide. Diagnostic kits for performing such methods may be constructed to include a first container means containing the antibody and a second container means having a conjugate of a binding partner of the antibody and a label.

In another aspect the invention features a hybridoma which produces an antibody having specific binding affinity to a SIRP polypeptide.

By "hybridoma" is meant an immortalized cell line which is capable of secreting an antibody, for example a SIRP antibody.

In preferred embodiments the SIRP antibody comprises a sequence of amino acids that is able to specifically bind a SIRP polypeptide.

Another aspect of the invention features a method of detecting the presence or amount of a compound capable of binding to a SIRP polypeptide. The method involves incubating the compound with a SIRP polypeptide and detecting the presence or amount of the compound bound to the SIRP polypeptide.

In preferred embodiments, the compound inhibits an activity of SIRP. The present invention also features compounds capable of binding and inhibiting SIRP polypeptide that are identified by methods described above.

In another aspect the invention features a method of screening potential agents useful for treatment of a disease or condition characterized by an abnormality in a signal transduction pathway that contains an interaction between a SIRP polypeptide and a natural binding partner (NBP). The method involves assaying potential agents for those able to promote or disrupt the interaction as an indication of a useful agent.

By "NBP" is meant a natural binding partner of a SIRP polypeptide that naturally associates with a SIRP polypeptide. The structure (primary, secondary, or tertiary) of the particular natural binding partner will influence the particular type of interaction between the SIRP polypeptide and the natural binding partner. For example, if the natural binding partner comprises a sequence of amino acids complementary to the SIRP polypeptide, covalent bonding may be a possible interaction. Similarly, other structural characteristics may allow for other corresponding interactions. The interaction is not limited to particular residues and specifically may involve phosphotyrosine, phosphoserine, or phosphothreonine residues. A broad range of sequences may be capable of interacting with SIRP polypeptides. One example of a natural binding partner may be SHP-2, which is described above. Other examples include, but are not limited to, SHP-1 and Grb2. Using techniques well known in the art, one may identify several natural binding partners for SIRP polypeptides such as by utilizing a two-hybrid screen.

By "screening" is meant investigating an organism for the presence or absence of a property. The process may include measuring or detecting various properties, including the level of signal transduction and the level of interaction between a SIRP polypeptide and a NBP.

By "disease or condition" is meant a state in an organism, e.g., a human, which is recognized as abnormal by members of the medicalcommunity. The disease or condition may be characterized by an abnormality in one or more signal transduction pathways in a cell wherein one of the components of the signal transduction pathway is either a SIRP polypeptide or a NBP. Specific diseases or disorders which might be treated or prevented, based upon the affected cells include cancers and diabetes.

In preferred embodiments, the methods described herein involve identifying a patient in need of treatment. Those skilled in the art will recognize that various techniques may be used to identify such patients.

By "abnormality" is meant an a level which is statistically different from the level observed in organisms not suffering from such a disease or condition and may be characterized as either an excess amount, intensity or duration of signal or a deficient amount, intensity or duration of signal. The abnormality in signal transduction may be realized as an abnormality in cell function, viability or differentiation state. The present invention is based in part on the determination that such abnormality in a pathway can be alleviated by action at the SHP-2-SIRP interaction site in the pathway. An abnormal interaction level may also either be greater or less than the normal level and may impair the normal performance or function of the organism. Thus, it is also possible to screen for agents that will be useful for treating a disease or condition, characterized by an abnormality in the signal transduction pathway, by testing compounds for their ability to affect the interaction between a SIRP polypeptide and SHP-2, since the complex formed by such interaction is part of the signal transduction pathway. However, the disease or condition may be characterized by an abnormality in the signal transduction pathway even if the level of interaction between the SIRP polypeptide and NBP is normal.

By "interact" is meant any physical association between polypeptides, whether covalent or non-covalent. This linkage can include many chemical mechanisms, for instance covalent binding, affinity binding, intercalation, coordinate binding and complexation. Examples of non-covalent bonds include electrostatic bonds, hydrogen bonds, and Van der Waals bonds. Furthermore, the interactions between polypeptides may either be direct or indirect. Thus, the association between two given polypeptides may be achieved with an intermediary agent, or several such agents, that connects the two proteins of interest (e.g., a SIRP polypeptide and SHP-2). Another example of an indirect interaction is the independent production, stimulation, or inhibition of both a SIRP polypeptide and SHP-2 by a regulatory agent. Depending upon the type of interaction present, various methods may be used to measure the level of interaction. For example, the strengths of covalent bonds are often measured in terms of the energy required to break a certain number of bonds (i.e., kcal/mol) Non-covalent interactions are often described as above, and also in terms of the distance between the interacting molecules. Indirect interactions may be described in a number of ways, including the number of intermediary agents involved, or the degree of control exercised over the SIRP polypeptide relative to the control exercised over SHP-2 or another NBP.

By "disrupt" is meant that the interaction between the SIRP polypeptide and SHP-2 or a NBP is reduced either by preventing expression of the SIRP polypeptide, or by preventing expression of SHP-2 or NBP, or by specifically preventing interaction of the naturally synthesized proteins or by interfering with the interaction of the proteins.

By "promote" is meant that the interaction between a SIRP polypeptide and SHP-2 or NBP is increased either by increasing expression of a SIRP polypeptide, or by increasing expression of SHP-2 or a NBP, or by decreasing the dephosphorylating activity of the corresponding regulatory PTP (or other phosphatase acting on other phosphorylated signaling components) by promoting interaction of the SIRP polypeptide and SHP-2 or NBP or by prolonging the duration of the interaction. Covalent binding can be promoted either by direct condensation of existing side chains or by the incorporation of external bridging molecules. Many bivalent or polyvalent linking agents are useful in coupling polypeptides, such as an antibody, to other molecules. For example, representative coupling agents can include organic compounds such as thioesters, carbodiimides, succinimide esters, diisocyanates, glutaraldehydes, diazobenzenes and hexamethylene diamines. This listing is not intended to be exhaustive of the various classes of coupling agents known in the art but, rather, is exemplary of the more common coupling agents. (See Killen and Lindstrom 1984, *J. Immunol.* 133:1335–2549; Jansen, F. K., et al., 1982, *Immunological Rev.* 62:185–216; and Vitetta et al., supra).

By "signal transduction pathway" is meant the sequence of events that involves the transmission of a message from an extracellular protein to the cytoplasm through a cell membrane. The signal ultimately will cause the cell to perform a particular function, for example, to uncontrollably proliferate and therefore cause cancer. Various mechanisms for the signal transduction pathway (Fry et al., Protein Science, 2:1785–1797, 1993) provide possible methods for measuring the amount or intensity of a given signal. Depending upon the particular disease associated with the abnormality in a signal transduction pathway, various symptoms may be detected. Those skilled in the art recognize those symptoms that are associated with the various other diseases described herein. Furthermore, since some adapter molecules recruit secondary signal transducer proteins towards the membrane, one measure of signal transduction is the concentration and localization of variousproteins and complexes. In addition, conformational changes that are involved in the transmission of a signal may be observed using circular dichroism and fluorescence studies.

In another aspect the invention features a method of diagnosis of an organism for a disease or condition characterized by an abnormality in a signal transduction pathway that contains an interaction between a SIRP polypeptide and SHP-2 or a NBP. The method involves detecting the level of interaction as an indication of said disease or condition.

By "organism" is meant any living creature. The term includes mammals, and specifically humans. Preferred organisms include mice, as the ability to treat or diagnose mice is often predictive of the ability to function in other organisms such as humans.

By "diagnosis" is meant any method of identifying a =symptom normally associated with a given disease or condition. Thus, an initial diagnosis may be conclusively established as correct by the use of additional confirmatory evidence such as the presence of other symptoms. Current classification of various diseases and conditions is constantly changing as more is learned about the mechanisms causing the diseases or conditions. Thus, the detection of an important symptom, such as the detection of an abnormal level of interaction between SIRP polypeptides and SHP-2 or NBPs may form the basis to define and diagnose a newly named disease or condition. For example, conventional cancers are classified according to the presence of a particular set of symptoms. However, a subset of these symptoms may both be associated with an abnormality in a particular signaling pathway, such as the $ras^{21}$ pathway and in the future these diseases may be reclassified as $ras^{21}$ pathway diseases regardless of the particular symptoms observed.

Yet another aspect of the invention features a method for treatment of an organism having a disease or condition characterized by an abnormality in a signal transduction pathway. The signal transduction pathway contains an interaction between a SIRP polypeptide and SHP-2 or a NBP and the method involves promoting or disrupting the interaction, including methods that target the SIRP:NBP interaction directly, as well as methods that target other points along the pathway.

By "dominant negative mutant protein" is meant a mutant protein that interferes with the normal signal transduction pathway. The dominant negative mutant protein contains the domain of interest (e.g., an SIRP polypeptide or SHP-2 or a NBP), but has a mutation preventing proper signaling, for example by preventing binding of a second domain from the same protein. One example of a dominant negative protein is described in Millauer et al., *Nature* Feb. 10, 1994. The agent is preferably a peptide which blocks or promotes interaction of the SIRP polypeptide and SHP-2 or another NBP. The peptide may be recombinant, purified, or placed in a pharmaceutically acceptable carrier or diluent.

An $EC_{50}$ or $IC_{50}$ of less than or equal to 100 $\mu$M is preferable, and even more preferably less than or equal to 50 $\mu$M, and most preferably less that or equal to 20 $\mu$M. Such lower $EC_{50}$'s or $IC_{50}$'s are advantageous since they allow lower concentrations of molecules to be used in vivo or in vitro for therapy or diagnosis. The discovery of molecules with such low $EC_{50}$'s and $IC_{50}$'s enables the design and synthesis of additional molecules having similar potency and effectiveness. In addition, the molecule may have an $EC_{50}$ or $IC_{50}$ less than or equal to 100 μM at one or more, but not all cells chosen from the group consisting of parathyroid cell, bone osteoclast, juxtaglomerular kidney cell, proximal tubule kidney cell, distal tubule kidney cell, cell of the thick ascending limb of Henle's loop and/or collecting duct, central nervous system cell, keratinocyte in the epidermis, parafollicular cell in the thyroid.(C-cell), intestinal cell, trophoblast in the placenta, platelet, vascular smooth muscle cell, cardiac atrial cell, gastrin-secreting cell, glucagon-secreting cell, kidney mesangial cell, mammary cell, beta cell, fat/adipose cell, immune cell and GI tract cell.

By "therapeutically effective amount" is meant an amount of a pharmaceutical composition having a therapeutically relevant effect. A therapeutically relevant effect relieves to some extent one or more symptoms of the disease or condition in the patient; or returns to normal either partially or completely one or more physiological or biochemical parameters associated with or causative of the disease or condition. Generally, a therapeutically effective amount is between about 1 nmole and 1 μmole of the molecule, depending on its $EC_{50}$ or $IC_{50}$ and on the age and size of the patient, and the disease associated with the patient.

In another aspect, the invention describes a polypeptide comprising a recombinant SIRP polypeptide or a unique fragment thereof. By "unique fragment," is meant an amino acid sequence present in a full-length SIRP polypeptide that is not present in any other naturally occurring polypeptide. Preferably, such a sequence comprises 6 contiguous amino acids present in the full sequence. More preferably, such a sequence comprises 12 contiguous amino acids present in the full sequence. Even more preferably, such a sequence comprises 18 contiguous amino acids present in the full sequence.

By "recombinant SIRP polypeptide" is meant to include a polypeptide produced by recombinant DNA techniques such that it is distinct from a naturally occurring polypeptide either in its location (e.g, present in a different cell or tissue than found in nature), purity or structure. Generally, such a recombinant polypeptide will be present in a cell in an amount different from that normally observed in nature.

In another aspect, the invention describes a recombinant cell or tissue containing a purified nucleic acid coding for a SIRP polypeptide. In such cells, the nucleic acid may be under the control of its genomic regulatory elements, or may be under the control of exogenous regulatory elements including an exogenous promoter. By "exogenous" it is meant a promoter that is not normally coupled in vivo transcriptionally to the coding sequence for the SIRP polypeptide.

In another aspect, the invention features a SIRP polypeptide binding agent able to bind to a SIRP polypeptide. The binding agent is preferably a purified antibody which recognizes an epitope present on a SIRP polypeptide. Other binding agents include molecules which bind to the SIRP polypeptide and analogous molecules which bind to a SIRP polypeptide.

By "purified" in reference to an antibody is meant that the antibody is distinct from naturally occurring antibody, such as in a purified form. Preferably, the antibody is provided as a homogeneous preparation by standard techniques. Uses of antibodies to the cloned polypeptide include those to be used as therapeutics, or as diagnostic tools.

In another aspect, the invention provides a nucleic acid molecule comprising a nucleotide sequence that encodes a polypeptide having the full length amino acid sequence set forth in SEQ ID NO:5, SEQ ID NO:6, SEQ ID NO:7, or SEQ ID NO:8 except that it lacks at least one of the domains selected from the group consisting of the extracellular Ig like domain, the transmembrane domain, and the SHP-2 binding domains. Such deletion mutants are useful in the design of assays for protein inhibitors. The nucleic acid molecules described above may be, for example, cDNA or genomic DNA and may be placed in a recombinant vector or expression vector. In such a vector, the nucleic acid preferably is operatively associated with the regulatory nucleotide sequence containing transcriptional and translational regulatory information that controls expression of the nucleotide sequence in a host cell.

Thus, the invention also provides a genetically engineered host cell containing any of the nucleotide sequences described herein and the nucleic acid preferably is operatively associated with the regulatory nucleotide sequence containing transcriptional and translational regulatory information that controls expression of the nucleotide sequence in a host cell. Such host cells may obviously be either prokaryotic or eukaryotic.

Other features and advantages of the invention will be apparent from the following description of the preferred embodiments thereof, and from the claims.

BRIEF DESCRIPTION OF THE FIGURES

FIG. 1 shows the deduced amino acid sequences of SIRP4 (SEQ ID NO: 6) and SIRP 5 (SEQ ID NO: 5). Identical amino acids are boxed. The putative signal sequence and the transmembrane region are indicated by thin and thick overlines, respectively. Three Ig-like domains are indicated by stippled overlines. Potential tyrosine phosphorylation sites are shown in bold, the C-terminal proline rich region is shaded. The location of oligonucleotides flanking the Ex region is indicated by stars.

FIG. 2 (SEQ ID NO: 14, residues 32 to 128 of SEQ ID NO: 6, residues 31–137 of SEQ ID NO: 5, SEQ ID NOS 15–26, respectively, in order of appearance) shows the alignment of extracellular regions including the first Ig-like domain of 15 SIRP family members. Ex1 shows the amino acids encoded by the initial PCR fragment that was used for screening and GST-fusion protein construction. Ex2–11 are derived from PCR and cDNA sequences, Ex 12–13 from genomic isolates. Numbering is according to FIG. 1.

FIG. 3 shows the alignment of amino acid sequences of human SIRP4 (SEQ ID NO: 6), mouse SIRP1 (SEQ ID NO: 5), human SIRPα1 (SEQ ID NO: 7) and mouse SIRPβ1 (SEQ ID NO: 8).

DESCRIPTION OF THE PREFERRED EMBODIMENTS

The present invention relates to SIRP polypeptides, nucleic acids encoding such polypeptides, cells, tissues and animals containing such nucleic acids, antibodies to such polypeptides, assays utilizing such polypeptides, and methods relating to all of the foregoing. Those skilled in the art will recognize that many of the methods described below in relation to SIRP1, SIRP4, SHP-2, SHP-1 and Grb2 could also be utilized with respect to the other members of this group.

Various other features and aspects of the invention are: Nucleic Acid Encoding A SIRP Polypeptide; A Nucleic Acid Probe for the Detection of SIRP; Probe Based Method And Kit For Detecting SIRP; DNA Constructs Comprising a SIRP Nucleic Acid Molecule and Cells Containing These Constructs; Purified SIRP Polypeptides; SIRP Antibody And Hybridoma; An Antibody Based Method And Kit For Detecting SIRP; Isolation of Compounds Which Interact With SIRP; Compositions; Disruption of Protein Complexes; Antibodies to Complexes; Pharmaceutical Formulations and Modes of Administration; Identification of Agents; Purification and Production of Complexes; Derivatives of Complexes; and Evaluation of Disorders.

All of these aspects and features are explained in detail with respect to another protein involved with signal transduction, PYK-2, in PCT publication WO 96/18738, which is incorporated herein by reference in its entirety, including any drawings. Those skilled in the art will readily appreciate that such description can be easily adapted to SIRP as well, and is equally applicable to the present invention.

For example, as disclosed in WO 96/18738, the nucleic acid molecules of the present invention may be cloned into a variety of vectors including those derived from plasmids, bacteriophage and viruses. Additionally, the nucleic acid molecules of the present invention may, as necessary, have restriction endonuclease recognition sites added to their 5'-end and/or 3'-ends. Examples of suitable plasmid vectors may include pBR322, pUC 118, pUC 119 and the like; suitable phage or bacteriophage vectors may include λgt10, λgt11, and the like; and suitable virus vectors may include pMAM-neo, pKRC and the like.

To express the nucleic acids of the present invention in a prokaryotic cell, it is necessary to operably link the nucleic acid molecules of the invention to a functional prokaryotic promoter. Such promoters may be either constitutive or, more preferably, regulatable (i.e., inducible or derepressible). Examples of constitutive promoters include the int promoter of bacteriophage λ, the bla promoter of the β-lactamase gene sequence of pBR322, and the CAT promoter of the chloramphenicol acetyl transferase gene sequence of pBR325, and the like. Examples of inducible prokaryotic promoters include the major right and left promoters of bacteriophage λ (PL and PR), the trp, recA lacZ, LacI, and gal promoters of $E.\ coli$, the α-amylase (Uhmanen et al., J. Bacteriol. 162:176–182'(1985)) and the ζ-28-specific promoters of $B.\ subtilis$ (Gilman et al., Gene sequence 32:11–20 (1984)), the promoters of the bacteriophages of Bacillus (Gryczan, In The Molecular Biology of the Bacilli, Academic Press, Inc., NY (1982)).

Preferred prokaryotic vectors include plasmids such as those capable of replication in $E.\ coli$ such as, for example, pBR322, ColE1, pSC101, pACYC 184, πVX. Such plasmids are, for example, disclosed by Sambrook (cf. Molecular A cloning: A Laboratory Manual, second edition, edited by Sambrook, Fritsch, & Maniatis, Cold Spring Harbor Laboratory, (1989)). Bacillus plasmids include pC194, pC221, pT127, and the like. Such plasmids are disclosed by Gryczan (In: The Molecular Biology of the Bacilli, Academic Press, NY (1982), pp. 307–329). Suitable Streptomyces plasmids include plJ101 (Kendall et al., J. Bacteriol. 169:4177–4183 (1987)), and streptomyces bacteriiophages such as φC31 (Chater et al., In: Sixth International Symposium on Actinomycetales. Biology, Akademiai Kaido, Budapest, Hungary (1986), pp. 45–54). Pseudomonas plasmids are reviewed by John et al., (Rev. Infect. Dis. 8:693–704 (1986)), and Izaki (J. Bacteriol. 33:729–742 (1978)).

Preferred eukaryotic plasmids include, for example, BPV, vaccinia, SV40, 2-micron circle, and the like, or their derivatives. Full-length cDNA sequences can be subcloned into the following mammalian expression vectors: pLSV; downstream the SV40 early promoter, PLXSN-retroviral vector; downstream the Mo-MuLV long terminal repeat; pRK5; downstream the CMV promoter.

Expression of the nucleic acid molecules of the present invention in eukaryotic hosts requires the use of eukaryotic regulatory regions. Such regions will, in general, include a promoter region sufficient to direct the initiation of RNA synthesis. Preferred eukaryotic promoters include, for example, the promoter of the mouse metallothionein I gene sequence (Hamer et al., J. Mol. Appl. Gene. 1:273–288 (1982)); the TK promoter of Herpes virus (McKnight, $Cell$ 31:355–365 (1982)); the SV40 early promoter (Benoist et al., Nature (London) 290:304–310 (1981)); the yeast gal4 gene sequence promoter (Johnston et al., Proc. Natl. Acad. Sci. (USA) 81:5951–5955 (1984)).

Host cells which may be used in the expression systems of the present invention are not strictly limited, provided that they are suitable for use in the expression of the SIRP peptide of interest. Suitable hosts may often include eukaryotic cells. Preferred eukaryotic hosts include for example, yeast, fungi, insect cells, mammalian cells either in vivo, or in tissue culture. Mammalian cells which may be useful as hosts include HeLa cells, cells of the fibroblastorigin such as a VERO or CHO-K1, or cells of lymphoid origin and their derivatives. Preferred mammalian host cells include PC12 cells, NIH3T3, SP2/O and J5581, as well as neuroblastoma cell lines such as IMR 332 which may provide better capacities for correct post-translational processing.

EXAMPLES

The examples below are non-limiting and are merely representative of various aspects and features of the procedures used to identify the full-length nucleic acid and amino acid sequences of a series of SIRP proteins. Experiments demonstrating SIRP expression, interaction and signaling activities are also provided.

Material and Methods
Cell Culture and Transient Expression

MM5/C1, Rat1-IR, A431 or human fibroblast cells were grown until confluency, starved for 18 hours in serum-free medium, and either left untreated or were POV—(1 mM sodium orthovanadate, 3 mM $H_2O_2$), insulin—(100 nM), EGF—(1 nM), or PDGF—(100 pM) stimulated for different time intervals as indicated. SIRP4, SHP-2 (Vogel, et al., $Science$ 259:1611–1614 (1994)) or SHP-2C463 A mutant (Stein-Gerlach, et al. $J.\ Biol.\ Chem.$ 270:24635–24637 (1995)) cDNAs were transiently cotransfected in BHK-IR, BHK-EGFR or BHK-βPDGFR cells using the calcium precipitation method (Chen, et al. $Mol,\ Cell.\ Biol.$ 7:2745–2752 (1987)). After stimulation, cells were lysed in buffer containing 50 mM HEPES, pH 7.5, 150 mM NaCl, 1% Triton X-100, 10% glycerol,. 1 mM POV, 1 mM EDTA, 1 mM PMSF, 1 mg/ml leupeptin, 1 mg/ml aprotinin.

Immunoprecipitation and Western Blotting

SHP-2 immunoprecipitations were performed with polyclonal anti-SHP-2 antibodies (Vogel, et al., $Science$ 259:1611–1614 (1994)). Overexpressed SIRP4 or endogenous SIRP4-like proteins were immunoprecipitated by polyclonal anti-Ex1 antibodies raised by immunizing rabbits with a GST-fusion protein containing the Ex1 fragment (FIG. 2). Western blots were labeled with monoclonal anti-phosphotyrosine antibodies 5E2 (Fendly, et al., $Cancer\ Res.$ 50:1550–1558 (1990)), and after stripping, reprobed with monoclonal anti-SHP-2 antibodies (Transduction Laboratories), or polyclonal anti-SIRP4-CT antibodies, raised against a GST-fusion protein containing the C-terminal part of SIRP4 (amino acids 336–503). For immunolabeling goat anti-mouse or -rabbit horseradish peroxidase conjugates (Bio-Rad) and the ECL detection system (Amersham) were used.

To obtain 293 cells stably expressing SIRP4 (293/SIRP4), cells were transfected with SIRP4 cDNA in PLXSN (Miller, et al. *Biotechniaues* 7:980–988 (1989)) using the calcium precipitation method, followed by selection with G418 (1 mg/ml). SIRP4 was immunoprecipitated from quiescent or POV-stimulated (1 mM) 293/SIRP4 cells with polyclonal anti-Ex1 antibodies. Subsequently, crude lysates of [$^{35}$S]-methionine labeled 293 cells expressing different SH2 domain containing proteins were added to the affinity matrix and incubated for 2 h at 4° C. The immunocomplexes were washed, separated by SDS-PAGE and analyzed by autoradiography.

Enzymatic Deglycosylation

To perform in vitro deglycosylation SHP-2 immunocomplexes or the 110 kDa protein preparation were first denatured in the presence of 1% SDS at 100° C. for 5 min. Deglycosylation was done in potassium phosphate buffer (40 mM, pH 7.0), containing 20 mM EDTA, 1% b-mercaptoethanol, 1% Triton X-100 and 0.5 Unit of Endoglycosidase F/N-Glycosidase F (Boehringer Mannheim) at 37° C. for 16 hours.

Protein Purification

Approximately $10^{10}$ Rat1-IR cells were used to purify the 110 kDa protein. Starved Rat1-IR cells were insulin-stimulated (100 nM) for 10 min, washed briefly with ice-cold hypotonic buffer containing 20 mM HEPES, pH 7.5, 1 mM POV, 1 mM EDTA, 1 mM PMSF, 1 mg/ml leupeptin, 1 mg/ml aprotinin, scraped into the same buffer and homogenized. Obtained cell extracts were pelleted at 1000 rpm for 15 min, and supeinatants were spun at 48.000 g for 1 hour. Membranes were solubilized in lysis buffer as described above. hIR was depleted from membrane extracts using an affinity column with monoclonal anti-hIR antibody 83–14 (Redemann et al., *Mol. Cell. Biol.* 12:491–498 (1992)), covalently coupled to Protein A-Sepharose beads (Pharmacia). Depleted extracts were applied onto a WGA-agarose 6 MB column (Sigma), and glycoproteins were eluted with 0.3 M N-acetyl-glucosamine in HNTG (20 mM HEPES (pH 7.5), 150 mM NaCl, 0.1% Triton X-100, 10% glycerol, 1 mM POV). After concentration protein extracts were applied onto an anti, phosphotyrosine antibody column (Sigma). Bound proteins were eluted with 20 mM phosphotyrosine in HNTG. The eluate was subjected to SDS-PAGE, proteins were transferred to a PVDF membrane (Millipore) and stained with Coomassie blue. The protein of 10 kD apparent molecular weight was microsequenced. The following five tryptic peptides were obtained: PIYSFIGGEHFPR (SEQ ID NO: 9), IVEPDTEIK (SEQ ID NO: 10), YGFSPR (SEQ ID NO: 11), IKEVAHVNLEVR (SEQ ID NO: 12), VAAGDSAT (SEQ ID NO: 13).

Biological Assays

To produce retroviruses expressing pLXSN, wild type SIRP4 and mutated SIRP4 constructs, BOSC 23 cells were transiently transfected by expression plasmids as described (Pear, et al. *Proc. Natl. Acad. Sci.* 90:8392–8396 (1993)). To obtain NIH3T3 cells stably expressing wild type SIRP4, SIRP4-4Y or SIRP4-DCT mutants subconfluent NIH3T3 cells ($10^5$ cells per 6 cm dish) were incubated with supernatants of transfected BOSC 23 cells for 4 h in the presence of Polybrene (4 mg/ml), followed by selection with G418 (1 mg/ml).

To perform focus formation assays cell lines 3T3/pLXSN, 3T3/SIRP4, 3T3/SIRP4-4Y or 3T3/SIRP4-DCT were superinfected for 4 hours with equal volumes of v-fms-virus supernatant ($10^5$ cells/6 cm dish). Cells were cultivated for 14 days in 4% FCS with medium change every second day. Cell foci were stained with Crystal violet (0.1% crystal violet, 30% methanol).

Example 1

Identification and Cloning of Signal Regulatory Proteins

Western blot of mammalian cells with anti-phosphotyrosine antibodies and anti-SHP-2 antibodies was used to identify tyrosine phosphorylated SHP-2 associated proteins.

Western blots containing anti-SHP-2 immunoprecipitates from starved or POV-treated mouse MM5/C1 mammary carcinoma, rat fibroblast Rat1-IR or human epidermal carcinoma A431 cells were incubated with anti-phosphotyrosine antibodies or anti-SHP-2 antibodies. Samples were deglycosylated with or treated without Endoglycosidase F/N-Glycosidase F (Endo.F/F). As a control, insulin-stimulated Rat1-IR cell lysates were immunoprecipitated with preimmune rabbit serum (aNS).

Samples from each purification step (i.e., solubilized crude membrane extract, hIR-depleted extracts, concentrated eluate from WGA-agarose beads, and eluate from anti-phosphotyrosine antibody column) were analyzed by 10% SDS-PAGE and visualized by silver staining and in Western blots using monoclonal anti-phosphotyrosine antibodies.

A major tyrosine phosphorylated protein was revealed in analysis of anti-SHP-2 immunoprecipitates from both pervanadate (POV) and growth factor stimulated cells. This phosphoprotein migrated at 120 kDa, 110 kDa and 90 kDa positions in mouse mammary tumor (MM5/C1) cells, Rat1 cells overexpressing the human insulin receptor (Rat1-IR), and human epidermoid carcinoma (A431) cells, respectively.

Upon in vitro deglycosylation, this glycoprotein was reduced to 65 kDa apparent molecular weight (MW) in all cases. This indicated that the same SHP-2 binding protein of 65 kDa was differentially glycosylated in a species specific manner.

In some cell lines such as A431, other tyrosine phosphorylated proteins in the 90–120 kDa range remained unaffected by the deglycosylation treatment. These proteins may represent Gab1 and/or the human homologue of the Drosophila DOS protein.

Insulin treated Rat1-IR were used to purify the 110 kDa SHP-2 binding glycoprotein using standard chromatography procedures. Approximately 4 mg of the glycoprotein that copurified with SHP-2 were obtained and subject to microsequence analysis. This yielded five peptide sequences: PIYSFIGGEHFPR (SEQ ID NO: 9), IVEPDTEIK (SEQ ID NO: 10), YGFSPR (SEQ ID NO: 11), IKEVAHVNLEVR (SEQ ID NO: 12), VAAGDSAT (SEQ ID NO: 13). Computer aided search in the EST database led to the identification of a 305 bp rat sequence (accession Nr.: H31804) and subsequent human cDNA fragment of 2 kb (EMBL databank, accession Nr.: U6701) containing matching and homologous sequences, respectively.

Specific primers flanking the very 5' portion of this sequence were used to amplify a 360 bp human DNA fragment (encoding Ex1 in FIG. 2) which was used to screen a human placenta cDNA library.

Several positive clones were isolated. One clone of 2.4 kb encoded a polypeptide of 503 amino acids designated SIRP4 (for signal Regulating Protein 4) with a calculated mass of 57,000. The deduced sequence identifies SIRP4 as a transmembrane protein with three Ig-like domains and a cytoplasmic portion containing four potential tyrosine phosphorylation sites and one proline-rich region.

A second cDNA clone, SIRP1, is also identified. This protein is highly homologous to SIRP4 within the Ig-like domains (Ig-1: 83%; Ig-2: 88%; Ig-3: 83%), but displays striking sequence divergence at the amino terminus and upstream of the transmembrane domain which gives rise to a shorter protein that still contains a transmembrane-like region but lacks the cytoplasmic C-terminal portion.

SIRP4 and SIRP1 are members of a novel protein family. This protein family has a variety of distinct sequence isoforms as evidenced by comparison of fifteen cDNA and genomic sequences within the first Ig-like domain (FIG. 2). Two major classes exist in SIRP family distinguished by the presence or absence of a cytoplasmic SHP-2 binding domain.

Example 2

Analyzing the Functions of SIRP4

SIRP4 binds to SHP-2 and serves as a substrate for SHP-2, IR, EGFR, and βPDGFR

The identity of SIRP4 as SHP-2 binding protein and substrate was confirmed by expression of the SIRP4 cDNA either alone or in combination with SHP-2 or an enzymatically inactive mutant SHP-2C463 A in BHK cells. BHK cells stably express human EGF-, insulin- or βPDGF receptors.

Immunoprecipitations were performed with a polyclonal antibody raised against a GST-fusion protein containing the extracellular Ex1 region (FIG. 2).

Western blots containing anti-SIRP4 immunoprecipitations from quiescent or ligand-stimulated BHK-IR, BHK-EGFR or BHK-5 PDGF cells were labeled with anti-phosphotyrosine, anti-SHP-2 and anti-SIRP4 antibodies, respectively.

Anti-SIRP4 immunoprecipitation revealed a tyrosine phosphorylated protein of 85–90 kDa upon ligand stimulation which associated with SHP-2.

The results suggested SIRP4 to be a direct substrate of SHP-2 since expression of the SHP-2 mutant SHP-2C463 A led to a significant increase in its phosphotyrosine content (even in starved cells) while coexpression of wt SHP-2 resulted in dephosphorylation. The MW of overexpressed SIRP4 matches that of the endogenous protein detected in SHP-2 immunoprecipitates from A431 cells.

Endogenous SIRP4-like proteins were immunoprecipitated from untreated or EGF-stimulated A431 cells, from quiescent or PDGF-treated human fibroblasts, or from starved or insulin-stimulated HBL-100 cells. As a control, ligand-stimulated cell lysates were immunoprecipitated with preimmune rabbit serum (aNS). Immunoblots were probed with monoclonal anti-phosphotyrosine and monoclonal anti-SHP-2 antibodies.

Polyclonal anti-Ex1 antibodies immunoprecipitate a protein of 85–90 kDa apparent MW from A431, HBL-100 tumor cells and human fibroblasts. This protein was tyrosine phosphorylated upon EGF, insulin or PDGF stimulation, respectively, and coprecipitated with SHP-2 in a ligand dependent manner.

These data indicate the existence of SIRP4 in several human cell lines where SIRP4 serves as a substrate for insulin-, EGF- and βPDGF receptors, binds SHP-2 in its tyrosine phosphorylated form and serves as a substrate for the phosphatase activity of SHP-2. The interaction of SHP-2 with SIRP4 likely involves one or both SH2 domains of SHP-2 as suggested by the requirement of phosphotyrosine residues and the abrogation of detectable association by mutation of critical residues in SHP-2 SH2 domains.

In vitro binding assays were performed to determine whether SIRP4 is able to interact with other SH2 domain-containing proteins. SIRP4-associated [$^{35}$S]-Methionine labeled proteins were resolved on SDS-PAGE and detected by autoradiography. The result shows that SIRP4 associates with both SHP-1 and Grb2 but not p85, Shc, Grb7, PLC-g, c-src, Nck, Vav, GAP, or ISGF-3.

A catalytically inactive SHP-1 mutant has recently been shown to bind an as yet unidentified tyrosine phosphorylated protein of 90–95 kDa in human 293 cells. This tyrosine phosphorylated protein is likely to be SIRP4 or one of its family members.

Effects of SIRP4 on Cell Growth and Transformation

To investigate the biological function of SIRP4, three stable transfectants of NIH3T3 cells were constructed to express wild type SIRP4 or SIRP4 mutants carrying either point mutations of the putative SHP-2 tyrosine binding sites (SIRP4-4Y) or a deletion of most of the cytoplasmic region (SIRP4-DCT).

Ligand-stimulated [$^3$H]-thymidine incorporation of NIH3T3 cells expressing empty vector (3T3/pLXSN), wild type SIRP4 (3T3/SIRP4), SIRP4-4Y (3T3/SIRP4-4Y) or SIRP4-DCT (3T3/SIRP4-DCT, amino acids 402–503 are deleted) mutants. Cells were grown to confluence in 24-well dishes (Nunc), starved for 24 h in DMEM/0.5% FCS, stimulated with different concentrations of insulin or EGF for 18 h, then incubated with 0.5 mCi [$^3$H]-thymidine per well for 4 h. Incorporation into DNA was determined as described (Redemann, et al. *Mol. Cell. Biol.* 12:491–498 (1992)).

Upon stimulation of cells with insulin, EGF and PDGF, control cells showed growth factor-induced DNA synthesis as measured by [$^3$H]-thymidine incorporation. Overexpression of SIRP4 led to a decrease of [$^3$H]-thymidine incorporation. In contrast, both SIRP4 mutants had nearly no effect on DNA synthesis. The observed inhibitory effect on DNA synthesis must be connected to SIRP4 tyrosine phosphorylation and/or its association with SHP-2 since wt SIRP4 became tyrosine phosphorylated and bound to SHP-2 upon ligand stimulation, and SIRP4 mutants did not.

SIRP4 effected growth inhibition upon insulin or EGF stimulation is correlated with reduced MAP kinase activation in 3T3/SIRP4 cells. 3T3/pLXSN, 3T3/SIRP4 or 3T3/SIRP4-4Y cells were starved for 18 hours in DMEM/0.50 FCS and stimulated with insulin or EGF for the time indicated. MAP kinase was detected in Western blots by using polyclonal erk1 and erk2 antibodies (Santa Cruz). In contrast, expression of SIRP4 mutants defective in SHP-2 binding had no effect on MAP kinase activation. Similar observations were made upon stimulation of the cells with PDGF.

These data strongly indicate that SIRP4 represents a novel regulatory element in the pathway that leads to MAP kinase activation.

We next determined the consequence of SIRP4 overexpression on oncogene mediated transformation of NIH3T3 cells. To examine the ability of SIRP4 to influence the formation of cell foci, subconfluent 3T3/pLXSN, 3T3/SIRP4, 3T3/SIRP4-4Y or 3T3/SIRP4-DCT cells were infected with v-fms virus supernatants.

As measured by focus formation, transformation by a v-fms retrovirus was significantly suppressed in cells overexpressing wt SIRP4 but not in cells expressing mutant SIRP4.

Previous reports have described certain SHP-2 binding proteins of 110–130 kDa apparent MW in mouse, rat or hamster cells. Tyrosine hyperphosphorylation of these proteins was observed when an enzymatically inactive SHP-2 mutant was overexpressed. In addition, disruption of SHP-2 function induced a variety of negative effects on growth factor-induced cellular signals. Our experiments strongly indicate that these proteins belong to the SIRP family and that the biological effects previously observed are due to the function of these SIRP proteins.

Without being bound by any theory, applicant proposes that tyrosine docking sites on SIRP proteins for either SHP-2 and/or other SH2 proteins such as SHP-1 or Grb2 play a significant role since the inhibitory effect of SIRP4 on NIH3T3 cell proliferation and transformation depends on phosphorylation of tyrosines.

One or both of the SHP phosphatases may tightly regulate the SIRP4 phosphorylation state.

SIRP4 may also act in its phosphorylated state as a "trapping" protein that sequesters SHP-2 from activated RTKs. The sequestion makes SHP-2 unavailable for other positive regulatory functions such as an adapter which recruits the Grb2-SOS complex to activated receptors. Such a function is supported by the observation that SHP-2 has higher affinity to the tyrosine phosphorylated form of SIRP4 than to autophosphorylated insulin and EGF receptors (Yamauchi, et al., *J. Biol. Chem.* 270:17716–17722, Yamauchi, et al. *J. Biol. Chem.* 270:14871–14874 (1995)).

A third possibility is based on the membrane-spanning structural features of the SIRP4 variant. The high degree of sequence diversity within the Ig-domains is reminiscent of immunoglobulin variable regions and suggests a role of extracellular determinants in the SIRP related signal transduction. Structurally defined interaction of SIRP with specific receptors, soluble ligands, extracellular matrix components or other factors may result in specific regulatory consequences for intracellular signaling events.

All publications referenced are incorporated by reference herein, including the nucleotide sequences, amino acid sequences, drawings and tables in each publication. All the compounds disclosed and referred to in the publications mentioned above are incorporated by reference herein, including those compounds disclosed and referred to in articles cited by the publications mentioned above.

Other embodiments of this invention are disclosed in the following claims. As will be obvious to those skilled in the art, may variations and modifications may be made without departing from the spirit and scope of the invention.

What is claimed is:

1. An isolated, enriched or purified nucleic acid molecule comprising a nucleotide sequence that
   (a) encodes a polypeptide having the full length amino acid sequence set forth in SEQ ID NO: 5, SEQ ID NO: 6, SEQ ID NO: 7, or SEQ ID NO: 8;
   (b) is the complement of the nucleotide sequence of (a); or
   (c) hybridizes under highly stringent conditions to the nucleotide molecule of (a) and encodes a naturally occurring SIRP polypeptide of at least 160 contiguous amino acids of the full-length sequence
      wherein said highly stringent conditions are at least as stringent as 50% formamide, 5×SSC (0.75 M NaCl, 0.075 M Sodium pyrophosphate, 5×Denhardt's solution, sonicated salmon sperm DNA (50 g/mL), 0.1% SDS, and 10% dextran sulfate at 42° C., with washes at 42° C. in 0.2×SSC and 0.1% SDS; and wherein said polypeptide binds to a receptor tyrosine kinase or a SH-2 domain bearing protein.

2. The nucleic acid molecule of claim 1, wherein said nucleic acid molecule is isolated, enriched, or purified from a mammal.

3. The nucleic acid molecule of claim 2, wherein said mammal is a human.

4. An isolated or purified nucleic acid vector comprising a nucleic acid molecule encoding (i) a polypeptide having an amino acid sequence selected from the group consisting of SEQ ID NO: 5, SEQ ID NO: 6, SEQ ID NO: 7, and SEQ ID NO: 8, and (ii) a promoter element,
   wherein said nucleic acid molecule and said promoter element are incorporated into said nucleic acid vector so that said nucleic acid molecule is effective to initiate transcription in a host cell; and wherein said polypeptide binds to a receptor tyrosine kinase or a SH-2 domain bearing protein.

5. An isolated, enriched or purified nucleic acid molecule comprising a nucleotide sequence that
   (a) encodes a polypeptide having an amino acid sequence that differs from the sequence set forth in SEQ ID NO: 5 or SEQ ID NO: 6 by lacking one or more, but not all, of the following segments of amino acid residues: 54–227, 250–330, 336–366, 367–398 of SEQ ID NO: 5, or 1–227, 250–336, 347–407, 408–503 of SEQ ID NO: 6, respectively;

(b) is the complement of the nucleotide sequence of (a);

(c) encodes a polypeptide having an amino acid sequence selected from the group consisting of amino acid residues 54–227 of SEQ ID NO: 5, 250–330 of SEQ ID NO: 5, 336–366 of SEQ ID NO: 5, 367–398 of SEQ ID NO: 5, 1–227 of SEQ ID NO: 6, 250–336 of SEQ ID NO: 6, 347–407 of SEQ ID NO: 6 and 408–503 of SEQ ID NO: 6; or (d) is the complement of the nucleotide sequence of (c), wherein said polypeptide binds to a receptor tyrosine kinase or a SH-2 domain bearing protein.

6. An isolated, enriched or purified nucleic acid molecule comprising a nucleotide sequence that (a) encodes a polypeptide having an amino acid sequence that differs from the sequence set forth in SEQ ID NO: 5, SEQ ID NO: 6, SEQ ID NO: 7, or SEQ ID NO: 8 by lacking at least one, but not more than two, of the domains selected from the group consisting of the extracellular domain, the transmembrane domain, and the SHP-2 binding domain; or (b) is the complement of the nucleotide sequence of (a), wherein said polypeptide binds to a receptor tyrosine kinase or a SH-2 domain bearing protein.

7. A recombinant cell comprising the nucleic acid molecule as in any one of claim 1, claim 5, or claim 6, wherein said nucleic acid molecule, is inserted into said cell.

8. The nucleic acid molecule of any one of claim 1, claim 5, or claim 6, wherein said nucleic acid molecule encodes a GST-fusion protein (Glutathione S Transferase-fusion protein).

9. An isolated, enriched or purified nucleic acid molecule comprising a nucleotide sequence set forth in nucleotides 41–1237 of SEQ ID NO: 1, nucleotides 13–1524 of SEQ ID NO: 2, nucleotides 59–1597 of SEQ ID NO: 3, or nucleotides 86–1261 of SEQ ID NO: 4.

10. The nucleic acid molecule of any one of claim 1, claim 4, or claim 6, further comprising restriction endonuclease recognition sites at the 5' end, the 3' end, or both the 5' and 3' ends, so that the nucleic acid molecule is manipulable to further comprise a nucleic acid sequence encoding a protein that promotes secretion, processing, or both secretion and processing of heterologous proteins encoded therefrom.

11. The nucleic acid molecule of claim 4, wherein said vector is selected from the group consisting of pBR322, pUC118, pUC119, ColE1, pSC101, pACYC184, pVX, pC194, pC221, pT127, p1J101, BPV, vaccinia, SV40, 2-micron circle, λgt10, λgt10, fC31, pMAM-neo, and pKRC.

12. The nucleic acid molecule of claim 4, wherein said promoter is selected from the group consisting of the int promoter of bacteriophage γ, the bla promoter of the β-lactamase gene sequence of pBR322, the CAT promoter of the chloramphenicol acetyl transferase gene sequence of pBR322, the major right or left promoters of bacteriophage γ, the trp, recA, lacZ, lacd or gal promoters of $E.\ coli$, the α-amylase specific promoter, and the sigma-28 specific promoter of $B.\ subtilis$.

13. The nucleic acid molecule of claim 4, wherein said host cell is a yeast cell, a fungi cell, an insect cell, a plant cell, or a mammalian cell, wherein said mammalian cell is either in vivo or in tissue culture.

14. The nucleic acid molecule of claim 13, wherein said mammalian cell is selected from the group consisting of a COS Cell, an HeLa cell, a VERO cell, a 3T3 cell, a, CHO-K1 cell, a 32D cell, an SP2/0 cell, a J558L cell, an IMR 332 cell and a PC12 cell.

15. The nucleic acid molecule of claim 4, wherein said host cell is eukaryotic, and wherein said promoter is selected from the group consisting of a mouse metallothionein I promoter, the TK promoter of Herpes virus, the SV40 early promoter and the yeast ga14 promoter.

16. The nucleic acid molecule of claim 4, wherein said vector is pLSV, pLXSN, or pRK5.

17. An isolated, enriched or purified nucleic acid molecule comprising a nucleotide sequence that (a) encodes a polypeptide having the full length amino acid sequence set forth in SEQ ID NO: 7, or SEQ ID NO: 8;

(b) is the complement of the nucleotide sequence of (a);

(c) hybridizes under highly stringent conditions to the nucleotide molecule of (a) or (b), and encodes a naturally occurring SIRP polypeptide of at least 160 contiguous amino acids of the full-length sequence, wherein said highly stringent conditions are at least as stringent as 50% formamide, 5×SSC (90.75 M NaCl, 0.075 M Sodium Pyrophosphate, 5×Denhardt's solution, sonicated salmon sperm DNA (50 g/ml), 0.1% SDS, and 10% dextran sulfate at 42° C., with washes at 42° C. in 0.2×SSC and 0.1 SDS); and wherein said polypeptide binds to a receptor tyrosine kinase or a SH-2 domain bearing protein.

* * * * *

SEQUENCE LISTING

<160> NUMBER OF SEQ ID NOS: 26

<210> SEQ ID NO 1
<211> LENGTH: 3804
<212> TYPE: DNA
<213> ORGANISM: Homo sapiens

<400> SEQUENCE: 1

```
cacagacgtt tggacagagc aggctcctaa ggtctccaga atgcccgtgc cagcctcctg      60
gccccacctt cctagtcctt tcctgctgat gacgctactg ctggggagac tcacaggagt     120
ggcaggtgag gacgagctac aggtgattca gcctgaaaag tccgtatcag ttgcagctgg     180
agagtcggcc actctgcgct gtgctatgac gtccctgatc cctgtggggc ccatcatgtg     240
gtttagagga gctggagcag gccgggaatt aatctacaat cagaaagaag gccacttccc     300
acgggtaaca actgtttcag aactcacaaa gagaaacaac ctgaactttt ccatcagcat     360
cagtaacatc accccagcag acgccggcac ctactactgt gtgaagttcc ggaaagggag     420
ccctgacgac gtggagttta gtctggagc aggcactgag ctgtctgtgc gcgccaaacc     480 ctctgcccc gtggtatcgg gccctgcggt gagggccaca cctgagcaca cagtgagctt     540
cacctgcgag tccatggct tctctcccag agacatcacc ctgaaatggt tcaaaaatgg     600
gaatgagctc tcagacttcc agaccaacgt ggacccgca ggagacagtg tgtcctacag     660
catccacagc acagccaggg tggtgctgac ccgtgggac gttcactctc aagtcatctg     720
cgagatggcc cacatcacct tgcaggggga ccctcttcgt gggactgcca acttgtctga     780
ggccatccga gttccaccca ccttggaggt tactcaacag cccatgaggg cagagaacca     840
ggcaaacgtc acctgccagg tgagcaattt ctaccccgg ggactacagc tgacctggtt     900
ggagaatgga aatgtgtccc ggacagaaac agcttcgacc ctcatagaga acaaggatgg    960
cacctacaac tggatgagct ggctcctggt gaacacctgt gcccacaggg acgatgtggt   1020
```

```
gctcacctgt caggtggagc atgatgggca gcaagcagtc agcaaaagct atgccctgga   1080
gatctcagca caccagaagg agcacggctc agatatcacc catgaaccag cgctggctcc   1140
tactgctcca ctcctcgtag ctctcctcct gggccccaag ctgctactgg tggttggtgt   1200
ctctgccatc tacatctgct ggaaacagaa ggcctgactg accctcagtc tctgctgcct   1260
cctcctttct tgagaagctc agcctgagag aaggagctgg cgagaacctt ccccacactc   1320
agctccaaac gcctcctctc ccaggtcatc tgcctgccca cacgctcctg ttccaccttc   1380
acaagaccat gatgccccaa agcagtgtct ctattcacgg tcctgagcag gggccatggg   1440
attgggctct gggcactgac tcatggcacc tccctagaag gtgagaaaca ctccaaatct   1500
aaacacacca ggacttctcc catccgtcgc cttgggactg ccataaacc acagactctc    1560 tccaggctct caagagttat cctgtcttct ggattcctgc ctaccccaac tcccccagcc   1620
ttgttgaggt tctctactgc ctcctgaata cacatgaacc cctataccaa ttttaagaaa   1680
aaaatgattc tctttcctct ttgtccaagc atcctatccc tcaaacccaa aagaaagaa    1740 gctctcccct tctctctgtc gatggagaca gtatttcttc tagtatcctg cagccttccc   1800
agtcctgctg cttgtggtag aaattgctgc cacagcccaa cattgaggag ccctcgatga   1860
ctgcccttta caactcatat tcagttctgc ctccaaaatg catgtgtcca cttacatgag   1920
atggtaaatg tttaacaatg gactttctga agggaaaaa ccaaaagctg ttttgcagtg    1980
cttgccaatt tctctagtgt aataactccc aacctgacca atttcagcac tgccaacagt   2040
taaacaacca gattcgaaga ttcctgaaat ttaacaattg gttttcaggg cccagtccaa   2100
gcctgctgct ggaaacctca gagttaaatc cctattctcc acacctctca cctccaccac   2160
ccctccctgt cccagccagc atcatctctt tggggaccac tcctctggct ttcattttc    2220 agccacagtg attctttgga aaagtcaaat catatcactt ctctgcttct tccccaacac   2280
agctgcatgg tcccgctctc cctccttcaa gtctctgctc aatgtcactt cattaaaggc   2340
ggccttctat aaactacctt gtataaaata ttatttattt tctctatccc ggcattctaa   2400
tttctcttat cctaattaat ttttctttag cccttatttt gatgagtatt atgccgaata   2460
caggcagccc tcacttttca tggccagtgc aagattgcaa aaagactgtg caacctgaaa   2520
cccaggaaag cagtctccat agtcaatcag aaaaacaatg atcattctgt gacctttacc   2580 atttttgtc aaaatattag aaactctcac actctcagtt acaaatgtag aggacaatga    2640
aaatataatg aaataaatat ttatttgtgc actacaattc aaagcattag aaacattgaa   2700
gtcaatggcg tttcttgtaa atgtatccag atgaggttgg aagagtgctt gaccttttg    2760 tatatttcta atatggagtg atatagtttg gctctgtgtc tccatccaaa tctcatctta   2820
aattgtaatc tgcatgtgtt gtgggaatgg gacctaggta ggaggtgact gaatacatgg   2880
gggcggactt ccccccttgct gttcttgtga tagtgagttc ataagatc tcagtgagtt    2940 ctcatgagat ctggtttttt gaaagtgtgt ggcaagtccc ccttcgctct ctctctctct   3000
ctccctcctg ccaccatgtg aagaaggtgc ctgcttcctt ttctccttcc accatggttg   3060
taagtttcct gaggcctccc agtcatgctt cctgttaagc ctgtggaact gtgagtccaa   3120
ttaaacctct tttattcata aaatatccag tttctgtag ttctttatag cagtgtgaga    3180
atgggctaat acacggagca agcatcgttc tttcattttt atttatttta tttttgaga    3240 tggagtttca cctattccc aggctggagt gcaatgtcgt gatcttggct cactgcaacc    3300
cccgcctcca gggttcaagt gattctcctg cctcagcctc ctgagtagct gggattacag   3360
```

-continued

| | |
|---|---|
| gcatgtacca ccacacccag ctaattttgt attttttagta gagatggggt ttctccatgt | 3420 |
| tgatcagact agtcttgaac tcccgacctc aggtgatcca cctgtcttgg cctcccaaag | 3480 |
| tgctgggatt acaggcatga gccaccatgc ctagccagca agcatcattt ctattatacc | 3540 |
| ttggtgtttg cctctttcta agtttggact agcttccaac atcttatccc ttgaattttc | 3600 |
| aatattgtgg aatcactcca gaagatcctt tcatgtgaag ttttttgctg gcatttcaac | 3660 |
| ctttgggaca tcttcagccc ttttattacc actcctctcc catttgtggc agtttgcgtt | 3720 |
| tactacctcc ctctggctgc ctatctgaag ttcctgcatc agggtctaca ttgccacagt | 3780 |
| caactatttg tacttctaga attc | 3804 |

<210> SEQ ID NO 2
<211> LENGTH: 2433
<212> TYPE: DNA
<213> ORGANISM: Homo sapiens

<400> SEQUENCE: 2

| | |
|---|---|
| cagccgcggc ccatggagcc cgccggcccg gcccccggcc gcctcgggcc gctgctctgc | 60 |
| ctgctgctcg ccgcgtcctg cgcctggtca ggagtggcgg gtgaggagga gctgcaggtg | 120 |
| attcagcctg acaagtccgt atcagttgca gctggagagt cggccattct gcactgcact | 180 |
| gtgacctccc tgatccctgt ggggcccatc cagtggttca gaggagctgg accagcccgg | 240 |
| gaattaatct acaatcaaaa agaaggccac ttccccgggg taacaactgt ttcagagtcc | 300 |
| acaaagagag aaaacatgga cttttccatc agcatcagta acatcacccc agcagatgcc | 360 |
| ggcacctact actgtgtgaa gttccggaaa gggagccctg acacggagtt taagtctgga | 420 |
| gcaggcactg agctgtctgt gcgtgccaaa ccctctgccc ccgtggtatc gggccctgcg | 480 |
| gcgagggcca cacctcagca cacagtgagc ttcacctgcg agtcccacgg cttctcaccc | 540 |
| agagacatca ccctgaaatg gttcaaaaat gggaatgagc tctcagactt ccagaccaac | 600 |
| gtggaccccg taggagagag cgtgtcctac agcatccaca gcacagccaa ggtggtgctg | 660 |
| acccgcgagg acgttcactc tcaagtcatc tgcgaggtgg cccacgtcac cttgcagggg | 720 |
| gaccctcttc gtgggactgc caacttgtct gagaccatcc gagttccacc caccttggag | 780 |
| gttactcaac agcccgtgag ggcagagaac caggtgaatg tcacctgcca ggtgaggaag | 840 |
| ttctaccccc agagactaca gctgacctgg ttggagaatg gaaacgtgtc ccggacagaa | 900 |
| acggcctcaa ccgttacaga gaacaaggat ggtacctaca actggatgag ctggctcctg | 960 |
| gtgaatgtat ctgcccacag ggatgatgtg aagctcacct gccaggtgga gcatgacggg | 1020 |
| cagccagcgg tcagcaaaag ccatgacctg aaggtctcag cccacccgaa ggagcagggc | 1080 |
| tcaaataccg ccgctgagaa cactggatct aatgaacgga acatctatat tgtggtgggt | 1140 |
| gtggtgtgca ccttgctggt ggccctactg atggcggccc tctacctcgt ccgaatcaga | 1200 |
| cagaagaaag cccagggctc cacttcttct acaaggttgc atgagcccga aagaatgcc | 1260 |
| agagaaataa cacaggacac aaatgatatc acatatgcag acctgaacct gcccaagggg | 1320 |
| aagaagcctg ctccccaggc tgcggagccc aacaaccacg cggagtatgc cagcattcag | 1380 |
| accagcccgc agcccgcgtc ggaggacacc ctcacctatg ctgacctgga catggtccac | 1440 |
| ctcaaccgga ccccccaagca gccggccccc aagcctgagc cgtccttctc agagtacgcc | 1500 |
| agcgtccagg tccgaggaa gtgaatggga ccgtggtttg ctctagcacc catctctacg | 1560 |
| cgctttcttg tcccacaggg agccgccgtg atgagcacga ccaacccagt tcccggaggg | 1620 |
| ctggggcggt gcaggctctg ggacccaggg gccagggtgg ctcttctctc cccacccctc | 1680 |

```
cttggctctc cagcacttcc tgggcagcca cggccccctc cccaacatt  gccacacacc    1740 tggaggctga cgttgccaaa ccagccaggg aaccaacctg ggaagtggcc agaactgcct    1800
ggggtccaag aactcttgtg cctccgtcca tcaccatgtg ggttttgaag accctcgact    1860
gcctccccga tgctccgaag cctgatcttc cagggtgggg aggagaaaat cccacctccc    1920
ctgacctcca ccacctccac caccaccacc accaccacca ccaccactac caccaccacc    1980
caactggggc tagagtgggg aagatttccc ctttagatca aactgcccct tccatggaaa    2040
agctggaaaa aaactctgga acccatatcc aggcttggtg aggttgctgc aacagtcct    2100 ggcctccccc atccctaggc aaagagccat gagtcctgga ggaggagagg accctccca    2160 aaggactgga agcaaaaccc tctgcttcct tgggtccctc caagactccc tggggcccaa    2220
ctgtgttgct ccaccccggac ccatctctcc cttctagacc tgagcttgcc cctccagcta    2280
gcactaagca acatctcgct gtaagcgcct gtaaattact gtgaaatgtg aaacgtgcaa    2340
tcttgaaact gaggtgttag aaaacttgat ctgtggtgtt ttgttttgtt ttttttctta    2400
aaacaacagc aacgtgaaaa aaaaaaaaaa aaa                                 2433

<210> SEQ ID NO 3
<211> LENGTH: 3645
<212> TYPE: DNA
<213> ORGANISM: Mus sp.

<400> SEQUENCE: 3
gcccgcctgc cgagcgcgct caccgccgct ctccctcctt gctctgcagc cgcggcccat      60
ggagcccgcc ggcgccctg gccgctagg gccgctgctg ctctgcctgc tgctctccgc      120
gtcctgtttc tgtacaggag tcacggggaa agaactgaag gtgactcagc ctgagaaatc     180
agtgtctgtt gctgctgggg attcgaccgt tctgaactgc actttgacct ccttgttgcc     240
ggtgggaccc attaagtggt acagaggagt aggcaaagcc ggctgtttga tctacagttt     300
cacaggagaa cactttcctc gagttacaaa tgtttcagat gctactaaga gaaacaatat     360
ggactttttc atccgtatca gtaatgtcac cccagaagat gccggtacct actactgtgt     420
gaagttccag aaaggaccat cagagcctga cacagaaata caatctggag ggggaacaga     480
ggtctatgta ctcgccaaac cttctccacc ggaggatccc cccaggagac aggggcatac     540
tgaccagaaa gtgaacttca cctgcaagtc tcatggcttc tctccccgga atatcacccct    600 gaagtggttc aaagatgggc aagaactcca cccttggag accaccgtga accctagtgg      660
aaagaatgtc tcctacaaca tctccagcac agtcagggtg gtactaaact ccatggatgt     720
tcattctaag gtcatctgcg aggtagccca catcaccttg gatagaagcc ctcttcgtgg     780
gattgctaac ctgtctaact tcatccgagt ttcacccacc gtgaaggtca cccaacagtc     840
cccgacgtca atgaaccagg tgaacctcac ctgccgggat gagaggttct accccgagga     900
tctccagctg atctggctgg agaatggaaa cgtatcacgg aatgacacgc caagaatct      960 cacaaagaac acgatggga cctataatta cacaagcttg ttcctggtga actcatctgc     1020
tcatagagag gacgtggtgt tcacgtgcca ggtgaagcac gaccaacagc cagcgatcac     1080
ccgaaaccat accgtgctgg gacttgccca ctcgagtgat caaggagca tgcaaacctt     1140 ccctggtaat aatgctaccc acaactggaa tgtcttcatc ggtgtgggcg tggcgtgtgc     1200
tttgctcgta gtcctgctga tggctgctct ctacctcctc cggatcaaac agaagaaagc     1260 caagggggtca acatcttcca cacggttgca cgagcccgag aagaacgcca gggaaataac    1320
```

-continued

```
ccaggtacag tctttgatcc aggacacaaa tgacatcaac gacatcacat acgcagacct    1380
gaatctccca agagaagga agcccgcacc cggctccctt gagttcctta acaaccacac    1440
agaatatgca agcattgaga caggcaaagt gcctaggcca gaggataccc tcacctatgc    1500
tgacctggac atggtccacc tcagccgggc acagccagcc cccaagcctg agccatcttt    1560
ctcagagtat gctagtgtcc aggtccagag gaagtgaatg gggctgtggt ctgtactagg    1620
ccccatcccc acaagttttc ttgtcctaca tggagtggcc atgacgagga catccagcca    1680
gccaatcctg tccccagaag gccaggtggc acgggtccta ggaccagggg taagggtggc    1740
ctttgtcttc cctccgtggc tcttcaacac ctcttgggca ccacgtcccc ttcttccgga    1800
ggctgggtct tgcagaacca gagggcgaac tggagaaatc tgcctggaat ccaagaagtg    1860
ttgtgcctcg gcccatcact cgtgggctcg atcctggtc ttggcaaccc caggttgcgt    1920
ccttgatgtt ccagagcttg gtcttctgtg tggagaagag ctcaccatct ctacccaact    1980
tgagctttgg gaccagactc cctttagatc aaaccgcccc atctgtggaa gaactacacc    2040
agaagtcgac aagttttcag ccaacagtgt ctggcctccc cacctcccag ctgactagc    2100
ctggggagaa ggaaccctct cctcctagac cagcagagac tccctgggca tgttcagtgt    2160
ggccccacct cccttccagt cccagcttgc ttcctccagc tagcactaac tcagcagcat    2220
cgctctgtgg acgcctgtaa attattgaga aatgtgaact gtgcagtctt aaagctaagg    2280
tgttagaaaa tttgatttat gctgtttagt tgttgttggg tttctttttct ttttaatttc    2340
ttttttcttt ttgatttttt ttctttccct taaaacaaca gcagccagca tcttggctct    2400
ttgtcatgtg ttgaatggtt gggtcttgtg aagtctgagg tctaacagtt tattgtcctg    2460
gaaggatttt cttacagcag aaacagattt ttttcaaatt cccagaatcc tgaggaccaa    2520
gaaggatccc tcagctgcta cttccagcac gcagcgtcac tgggacgaac caggccctgt    2580
tcttacaagg ccacatggcg ggcctttgcc tccatggcta ctgtggtaag tgcagccttg    2640
tctgacccaa tgctgaccta atgttggcca ttccacattg aggggacaag gtcagtgatg    2700
ccccccttgg ctcacaagca cttcagaggc atgcagagag aagggacact cgtccagctc    2760
tctgaggtaa tcagtgcaag gaggagtccg ttttttgcca gcaaacctca gcaggatcac    2820
actggaacag aacctggtca tacctgtgac aacacagctg tgagccaggg caaaccaccc    2880
actgtcactg gctcgagagt ctgggagagc tctgacccga cacccttaa actggatgcc    2940
ggggcctggc tgggcaatgc caagtggtta tggcaaccct gactatctgg tcttaacatg    3000
tagctcagga agtggaggcg ctaatgtccc caatccctgg ggattcctga ttccagctat    3060
tcatgtaagc agagccaacc tgcctatttc tgtagggtgc gactgggatg ttaggagcac    3120
agcaaggacc cagctctgta gggctggtga cctgataccct tctcataatg gcatctagaa    3180
gttaggctga gttgcctcac tggcccagca aaccagaact tgtctttggc cgggccatgt    3240
tcttgggctg tcttctaatt ccaaagggtt ggttggtaaa gctccacccc cttctcctct    3300
gcctaaagac ataacatgtg tatacacaca cgggtgtata gatgagttaa agaatgtcc    3360
tcgctggcat cctaattttg tcttaagttt ttttggaggg agaaaggaac aaggcaaggg    3420
aagatgtgta gctttggctt taaccaggca gcctgggggc tcccaagcct atggaaccct    3480
ggtacaaaga agagaacaga agcgccctgt gaggagtggg atttgttttt ctgtagacca    3540
gatgagaagg aaacaggccc tgttttgtac atagttgcaa cttaaaattt ttggcttgca    3600
aaatattttt gtaataaaga tttctgggta acaataaaaa aaaaa           3645
```

<210> SEQ ID NO 4
<211> LENGTH: 2020
<212> TYPE: DNA
<213> ORGANISM: Mus sp.

<400> SEQUENCE: 4

| | | | | | |
|---|---|---|---|---|---|
| ccctcactaa | agggaacaaa | agctggagct | ccaccgcggt | ggcggccgct ctagaactag | 60 |
| tggatccccc | gggctgcagg | caaccatgct | tctcctagat | gcctggaccc acattcctca | 120 |
| ctgtgtcctg | ctgttgatcc | tgcttctggg | acttaaagga | gcagctatga gagagctgaa | 180 |
| ggtgatccaa | cctgttaaat | catttttgt | tggtgctgga | gggtcagcca ctctgaactg | 240 |
| cacagtgaca | tctctcctcc | ctgtggggcc | catgaggtgg | tacaggggta taggacaaag | 300 |
| tcgactcttg | atatactcgt | tcacaggaga | aggcttcccc | agaataacaa atacttcaga | 360 |
| tactacaaag | agaaacaaca | tggacttttc | catccgtatc | agtaatgtca ctcctgctga | 420 |
| ttcgggtacc | tactactgtg | tgaagttcca | gagaggacca | tcagactttt acactgagat | 480 |
| tcagtctgga | ggtggcactg | agttgtcagt | acttgctaaa | ccatcttcac ctatggtctc | 540 |
| cggtcctgca | gccagagctg | tccctcagca | gacagtgacc | tttacatgca gatcccatgg | 600 |
| attctttccg | cggaacctca | cgctgaagtg | gttcaagaat | ggagatgaga tctctcactt | 660 |
| ggaaacttct | gtgaaccgg | aagaaacaag | tgtctcctat | agagtttcca gcacagtcca | 720 |
| ggtggtgttg | aacctaggg | atgtccgctc | tcagatcatc | tgtgaagtgg atcatgtcac | 780 |
| tttagatcga | gcccctctca | gagggattgc | tcacatctct | gagttcattc aagttccacc | 840 |
| caccctggag | atccgccagc | agccaacaat | ggtttggaat | gtgataaatg ttacctgcca | 900 |
| aatacagaag | ttctatcctc | caagttttca | gttgacctgg | ttagagaatg gaaatatatc | 960 |
| ccggagagaa | gtaccttta | cacttacagt | aaacaaggat | ggaacttaca actggatcag | 1020 |
| ctgtctcttg | gtgaacatat | ctgcccttga | ggagaacatg | gtagtgacat gccaggttga | 1080 |
| gcatgatgga | caagcagaag | tcattgaaac | ccatactgtg | gtggtcactg aacatcagag | 1140 |
| agtgaaaggt | actgctacca | agtctggtga | ggtcttcacc | ccaccttat gtctaaatgt | 1200 |
| aaattgggct | ttatttttta | tgtataaggt | aacattcttg | attattgtag cattatcctg | 1260 |
| acaactacaa | agtaaaatgt | taacgtcata | tttcattccc | aacttctcac acgtctcaca | 1320 |
| tatctttcca | ctaatagatt | aaatagttaa | gaatggaagg | tatcatcaaa ttccagtatc | 1380 |
| ttgccccttc | cctgttttac | ctaacatttg | tgaacatcct | tatgctcatg tgtttccttt | 1440 |
| accatatctt | tactgactcc | attacatttt | agatatttcc | taaatatagt gtcctaatgg | 1500 |
| agtgaaattt | caacgggtca | cctgacaacc | tgtttgtaca | cacacacaca cacacacaca | 1560 |
| cacacacaca | cacacagcat | atgatctgga | ctaatgaaat | aaaggaaaat caaatgtcca | 1620 |
| ttggagcact | gctatcacta | aggtataagg | aaaacttgct | agcaaagtat ttcttttcaa | 1680 |
| cttgttacga | tgctagcagt | tagtttgcat | tagattggac | ccatttatgt gaatatcttt | 1740 |
| ttccttctct | taaacaaca | aaaagatcc | tcaactccag | tgacttttga aaaactcatg | 1800 |
| ttccttggca | tccctccttt | gctgtgagtt | cattggctgg | ataaacactg ggtcgcctaa | 1860 |
| ttatctataa | atatgccagt | taaaaatgtc | aaggttagaa | agcatcagtc catacagtgc | 1920 |
| aaatatagtc | cacagtgggt | gctcaggtaa | atcatgatat | tttcatttaa aatatacatt | 1980 |
| caataaaatt | aactgtagtt | caaaaaaaaa | aaaaaaaaa | | 2020 |

<210> SEQ ID NO 5
<211> LENGTH: 398
<212> TYPE: PRT

-continued

<213> ORGANISM: Homo sapiens

<400> SEQUENCE: 5

```
Met Pro Val Pro Ala Ser Trp Pro His Leu Pro Ser Pro Phe Leu Leu
 1               5                  10                  15

Met Thr Leu Leu Leu Gly Arg Leu Thr Gly Val Ala Gly Glu Asp Glu
            20                  25                  30

Leu Gln Val Ile Gln Pro Glu Lys Ser Val Ser Val Ala Ala Gly Glu
        35                  40                  45

Ser Ala Thr Leu Arg Cys Ala Met Thr Ser Leu Ile Pro Val Gly Pro
    50                  55                  60

Ile Met Trp Phe Arg Gly Ala Gly Ala Gly Arg Glu Leu Ile Tyr Asn
65                  70                  75                  80

Gln Lys Glu Gly His Phe Pro Arg Val Thr Thr Val Ser Glu Leu Thr
                85                  90                  95

Lys Arg Asn Asn Leu Asn Phe Ser Ile Ser Ile Ser Asn Ile Thr Pro
            100                 105                 110

Ala Asp Ala Gly Thr Tyr Tyr Cys Val Lys Phe Arg Lys Gly Ser Pro
        115                 120                 125

Asp Asp Val Glu Phe Lys Ser Gly Ala Gly Thr Glu Leu Ser Val Arg
    130                 135                 140

Ala Lys Pro Ser Ala Pro Val Val Ser Gly Pro Ala Val Arg Ala Thr
145                 150                 155                 160

Pro Glu His Thr Val Ser Phe Thr Cys Glu Ser His Gly Phe Ser Pro
                165                 170                 175

Arg Asp Ile Thr Leu Lys Trp Phe Lys Asn Gly Asn Glu Leu Ser Asp
            180                 185                 190

Phe Gln Thr Asn Val Asp Pro Ala Gly Asp Ser Val Ser Tyr Ser Ile
        195                 200                 205

His Ser Thr Ala Arg Val Val Leu Thr Arg Gly Asp Val His Ser Gln
    210                 215                 220

Val Ile Cys Glu Met Ala His Ile Thr Leu Gln Gly Asp Pro Leu Arg
225                 230                 235                 240

Gly Thr Ala Asn Leu Ser Glu Ala Ile Arg Val Pro Pro Thr Leu Glu
                245                 250                 255

Val Thr Gln Gln Pro Met Arg Ala Glu Asn Gln Ala Asn Val Thr Cys
            260                 265                 270

Gln Val Ser Asn Phe Tyr Pro Arg Gly Leu Gln Leu Thr Trp Leu Glu
        275                 280                 285

Asn Gly Asn Val Ser Arg Thr Glu Thr Ala Ser Thr Leu Ile Glu Asn
    290                 295                 300

Lys Asp Gly Thr Tyr Asn Trp Met Ser Trp Leu Leu Val Asn Thr Cys
305                 310                 315                 320

Ala His Arg Asp Asp Val Val Leu Thr Cys Gln Val Glu His Asp Gly
                325                 330                 335

Gln Gln Ala Val Ser Lys Ser Tyr Ala Leu Glu Ile Ser Ala His Gln
            340                 345                 350

Lys Glu His Gly Ser Asp Ile Thr His Glu Pro Ala Leu Ala Pro Thr
        355                 360                 365

Ala Pro Leu Leu Val Ala Leu Leu Leu Gly Pro Lys Leu Leu Leu Val
    370                 375                 380

Val Gly Val Ser Ala Ile Tyr Ile Cys Trp Lys Gln Lys Ala
385                 390                 395
```

```
<210> SEQ ID NO 6
<211> LENGTH: 503
<212> TYPE: PRT
<213> ORGANISM: Homo sapiens

<400> SEQUENCE: 6
```

| | | | | | | | | | | | | | | | |
|---|---|---|---|---|---|---|---|---|---|---|---|---|---|---|---|
|Met|Glu|Pro|Ala|Gly|Pro|Ala|Pro|Gly|Arg|Leu|Gly|Pro|Leu|Leu|Cys|
|1| | | |5| | | | |10| | | | |15| |
|Leu|Leu|Leu|Ala|Ala|Ser|Cys|Ala|Trp|Ser|Gly|Val|Ala|Gly|Glu|Glu|
| | | | |20| | | | |25| | | | |30| |
|Glu|Leu|Gln|Val|Ile|Gln|Pro|Asp|Lys|Ser|Val|Ser|Val|Ala|Ala|Gly|
| | | | |35| | | | |40| | | | |45| |
|Glu|Ser|Ala|Ile|Leu|His|Cys|Thr|Val|Thr|Ser|Leu|Ile|Pro|Val|Gly|
| |50| | | | |55| | | | |60| | | | |
|Pro|Ile|Gln|Trp|Phe|Arg|Gly|Ala|Gly|Pro|Ala|Arg|Glu|Leu|Ile|Tyr|
|65| | | | |70| | | | |75| | | | |80|
|Asn|Gln|Lys|Glu|Gly|His|Phe|Pro|Arg|Val|Thr|Thr|Val|Ser|Glu|Ser|
| | | | |85| | | | |90| | | | |95| |
|Thr|Lys|Arg|Glu|Asn|Met|Asp|Phe|Ser|Ile|Ser|Ile|Ser|Asn|Ile|Thr|
| | | | |100| | | | |105| | | | |110| |
|Pro|Ala|Asp|Ala|Gly|Thr|Tyr|Tyr|Cys|Val|Lys|Phe|Arg|Lys|Gly|Ser|
| | | | |115| | | | |120| | | | |125| |
|Pro|Asp|Thr|Glu|Phe|Lys|Ser|Gly|Ala|Gly|Thr|Glu|Leu|Ser|Val|Arg|
| |130| | | | |135| | | | |140| | | | |
|Ala|Lys|Pro|Ser|Ala|Pro|Val|Val|Ser|Gly|Pro|Ala|Ala|Arg|Ala|Thr|
|145| | | | |150| | | | |155| | | | |160|
|Pro|Gln|His|Thr|Val|Ser|Phe|Thr|Cys|Glu|Ser|His|Gly|Phe|Ser|Pro|
| | | | |165| | | | |170| | | | |175| |
|Arg|Asp|Ile|Thr|Leu|Lys|Trp|Phe|Lys|Asn|Gly|Asn|Glu|Leu|Ser|Asp|
| | | | |180| | | | |185| | | | |190| |
|Phe|Gln|Thr|Asn|Val|Asp|Pro|Val|Gly|Glu|Ser|Val|Ser|Tyr|Ser|Ile|
| | | | |195| | | | |200| | | | |205| |
|His|Ser|Thr|Ala|Lys|Val|Val|Leu|Thr|Arg|Glu|Asp|Val|His|Ser|Gln|
| |210| | | | |215| | | | |220| | | | |
|Val|Ile|Cys|Glu|Val|Ala|His|Val|Thr|Leu|Gln|Gly|Asp|Pro|Leu|Arg|
|225| | | | |230| | | | |235| | | | |240|
|Gly|Thr|Ala|Asn|Leu|Ser|Glu|Thr|Ile|Arg|Val|Pro|Pro|Thr|Leu|Glu|
| | | | |245| | | | |250| | | | |255| |
|Val|Thr|Gln|Gln|Pro|Val|Arg|Ala|Glu|Asn|Gln|Val|Asn|Val|Thr|Cys|
| | | | |260| | | | |265| | | | |270| |
|Gln|Val|Arg|Lys|Phe|Tyr|Pro|Gln|Arg|Leu|Gln|Leu|Thr|Trp|Leu|Glu|
| | | | |275| | | | |280| | | | |285| |
|Asn|Gly|Asn|Val|Ser|Arg|Thr|Glu|Thr|Ala|Ser|Thr|Val|Thr|Glu|Asn|
| |290| | | | |295| | | | |300| | | | |
|Lys|Asp|Gly|Thr|Tyr|Asn|Trp|Met|Ser|Trp|Leu|Leu|Val|Asn|Val|Ser|
|305| | | | |310| | | | |315| | | | |320|
|Ala|His|Arg|Asp|Asp|Val|Lys|Leu|Thr|Cys|Gln|Val|Glu|His|Asp|Gly|
| | | | |325| | | | |330| | | | |335| |
|Gln|Pro|Ala|Val|Ser|Lys|Ser|His|Asp|Leu|Lys|Val|Ser|Ala|His|Pro|
| | | | |340| | | | |345| | | | |350| |
|Lys|Glu|Gln|Gly|Ser|Asn|Thr|Ala|Ala|Glu|Asn|Thr|Gly|Ser|Asn|Glu|
| | | | |355| | | | |360| | | | |365| |
|Arg|Asn|Ile|Tyr|Ile|Val|Val|Gly|Val|Val|Cys|Thr|Leu|Leu|Val|Ala|
| |370| | | | |375| | | | |380| | | | |

```
Leu Leu Met Ala Ala Leu Tyr Leu Val Arg Ile Arg Gln Lys Lys Ala
385                 390                 395                 400

Gln Gly Ser Thr Ser Ser Thr Arg Leu His Glu Pro Glu Lys Asn Ala
            405                 410                 415

Arg Glu Ile Thr Gln Asp Thr Asn Asp Ile Thr Tyr Ala Asp Leu Asn
            420                 425                 430

Leu Pro Lys Gly Lys Lys Pro Ala Pro Gln Ala Ala Glu Pro Asn Asn
            435                 440                 445

His Thr Glu Tyr Ala Ser Ile Gln Thr Ser Pro Gln Pro Ala Ser Glu
            450                 455                 460

Asp Thr Leu Thr Tyr Ala Asp Leu Asp Met Val His Leu Asn Arg Thr
465                 470                 475                 480

Pro Lys Gln Pro Ala Pro Lys Pro Glu Pro Ser Phe Ser Glu Tyr Ala
            485                 490                 495

Ser Val Gln Val Pro Arg Lys
            500

<210> SEQ ID NO 7
<211> LENGTH: 512
<212> TYPE: PRT
<213> ORGANISM: Mus sp.

<400> SEQUENCE: 7

Met Glu Pro Ala Gly Ala Pro Gly Arg Leu Gly Pro Leu Leu Leu Cys
1               5                   10                  15

Leu Leu Leu Ser Ala Ser Cys Phe Cys Thr Gly Val Thr Gly Lys Glu
            20                  25                  30

Leu Lys Val Thr Gln Pro Glu Lys Ser Val Ser Val Ala Ala Gly Asp
            35                  40                  45

Ser Thr Val Leu Asn Cys Thr Leu Thr Ser Leu Leu Pro Val Gly Pro
        50                  55                  60

Ile Lys Trp Tyr Arg Gly Val Gly Lys Ala Gly Cys Leu Ile Tyr Ser
65              70                  75                  80

Phe Thr Gly Glu His Phe Pro Arg Val Thr Asn Val Ser Asp Ala Thr
                85                  90                  95

Lys Arg Asn Asn Met Asp Phe Ser Ile Arg Ile Ser Asn Val Thr Pro
            100                 105                 110

Glu Asp Ala Gly Thr Tyr Tyr Cys Val Lys Phe Gln Lys Gly Pro Ser
            115                 120                 125

Glu Pro Asp Thr Glu Ile Gln Ser Gly Gly Thr Glu Val Tyr Val
            130                 135                 140

Leu Ala Lys Pro Ser Pro Pro Glu Asp Pro Arg Arg Gln Gly His
145                 150                 155                 160

Thr Asp Gln Lys Val Asn Phe Thr Cys Lys Ser His Gly Phe Ser Pro
            165                 170                 175

Arg Asn Ile Thr Leu Lys Trp Phe Lys Asp Gly Gln Glu Leu His Pro
            180                 185                 190

Leu Glu Thr Thr Val Asn Pro Ser Gly Lys Asn Val Ser Tyr Asn Ile
            195                 200                 205

Ser Ser Thr Val Arg Val Val Leu Asn Ser Met Asp Val His Ser Lys
        210                 215                 220

Val Ile Cys Glu Val Ala His Ile Thr Leu Asp Arg Ser Pro Leu Arg
225                 230                 235                 240

Gly Ile Ala Asn Leu Ser Asn Phe Ile Arg Val Ser Pro Thr Val Lys
```

```
                245                 250                 255
Val Thr Gln Gln Ser Pro Thr Ser Met Asn Gln Val Asn Leu Thr Cys
                260                 265                 270

Arg Asp Glu Arg Phe Tyr Pro Glu Asp Leu Gln Leu Ile Trp Leu Glu
                275                 280                 285

Asn Gly Asn Val Ser Arg Asn Asp Thr Pro Lys Asn Leu Thr Lys Asn
            290                 295                 300

Thr Asp Gly Thr Tyr Asn Tyr Thr Ser Leu Phe Leu Val Asn Ser Ser
305                 310                 315                 320

Ala His Arg Glu Asp Val Val Phe Thr Cys Gln Val Lys His Asp Gln
                325                 330                 335

Gln Pro Ala Ile Thr Arg Asn His Thr Val Leu Gly Leu Ala His Ser
                340                 345                 350

Ser Asp Gln Gly Ser Met Gln Thr Phe Pro Gly Asn Asn Ala Thr His
                355                 360                 365

Asn Trp Asn Val Phe Ile Gly Val Gly Val Ala Cys Ala Leu Leu Val
                370                 375                 380

Val Leu Leu Met Ala Ala Leu Tyr Leu Leu Arg Ile Lys Gln Lys Lys
385                 390                 395                 400

Ala Lys Gly Ser Thr Ser Ser Thr Arg Leu His Glu Pro Glu Lys Asn
                405                 410                 415

Ala Arg Glu Ile Thr Gln Val Gln Ser Leu Ile Gln Asp Thr Asn Asp
                420                 425                 430

Ile Asn Asp Ile Thr Tyr Ala Asp Leu Asn Leu Pro Lys Arg Arg Lys
                435                 440                 445

Pro Ala Pro Gly Ser Leu Glu Phe Leu Asn Asn His Thr Glu Tyr Ala
                450                 455                 460

Ser Ile Glu Thr Gly Lys Val Pro Arg Pro Glu Asp Thr Leu Thr Tyr
465                 470                 475                 480

Ala Asp Leu Asp Met Val His Leu Ser Arg Ala Gln Pro Ala Pro Lys
                485                 490                 495

Pro Glu Pro Ser Phe Ser Glu Tyr Ala Ser Val Gln Val Gln Arg Lys
                500                 505                 510

<210> SEQ ID NO 8
<211> LENGTH: 391
<212> TYPE: PRT
<213> ORGANISM: Mus sp.

<400> SEQUENCE: 8

Met Leu Leu Leu Asp Ala Trp Thr His Ile Pro His Cys Val Leu Leu
1               5                   10                  15

Leu Ile Leu Leu Leu Gly Leu Lys Gly Ala Ala Met Arg Glu Leu Lys
            20                  25                  30

Val Ile Gln Pro Val Lys Ser Phe Val Gly Ala Gly Gly Ser Ala
            35                  40                  45

Thr Leu Asn Cys Thr Val Thr Ser Leu Leu Pro Val Gly Pro Met Arg
        50                  55                  60

Trp Tyr Arg Gly Ile Gly Gln Ser Arg Leu Leu Ile Tyr Ser Phe Thr
65                  70                  75                  80

Gly Glu Gly Phe Pro Arg Ile Thr Asn Thr Ser Asp Thr Thr Lys Arg
                85                  90                  95

Asn Asn Met Asp Phe Ser Ile Arg Ile Ser Asn Val Thr Pro Ala Asp
                100                 105                 110
```

```
Ser Gly Thr Tyr Tyr Cys Val Lys Phe Gln Arg Gly Pro Ser Asp Phe
        115                 120                 125

Tyr Thr Glu Ile Gln Ser Gly Gly Thr Glu Leu Ser Val Leu Ala
130                 135                 140

Lys Pro Ser Ser Pro Met Val Ser Gly Pro Ala Ala Arg Ala Val Pro
145                 150                 155                 160

Gln Gln Thr Val Thr Phe Thr Cys Arg Ser His Gly Phe Phe Pro Arg
                    165                 170                 175

Asn Leu Thr Leu Lys Trp Phe Lys Asn Gly Asp Glu Ile Ser His Leu
            180                 185                 190

Glu Thr Ser Val Glu Pro Glu Thr Ser Val Ser Tyr Arg Val Ser
        195                 200                 205

Ser Thr Val Gln Val Val Leu Glu Pro Arg Asp Val Arg Ser Gln Ile
    210                 215                 220

Ile Cys Glu Val Asp His Val Thr Leu Asp Arg Ala Pro Leu Arg Gly
225                 230                 235                 240

Ile Ala His Ile Ser Glu Phe Ile Gln Val Pro Pro Thr Leu Glu Ile
                245                 250                 255

Arg Gln Gln Pro Thr Met Val Trp Asn Val Ile Asn Val Thr Cys Gln
                260                 265                 270

Ile Gln Lys Phe Tyr Pro Pro Ser Phe Gln Leu Thr Trp Leu Glu Asn
            275                 280                 285

Gly Asn Ile Ser Arg Arg Glu Val Pro Phe Thr Leu Thr Val Asn Lys
        290                 295                 300

Asp Gly Thr Tyr Asn Trp Ile Ser Cys Leu Leu Val Asn Ile Ser Ala
305                 310                 315                 320

Leu Glu Glu Asn Met Val Val Thr Cys Gln Val Glu His Asp Gly Gln
                325                 330                 335

Ala Glu Val Ile Glu Thr His Thr Val Val Thr Glu His Gln Arg
            340                 345                 350

Val Lys Gly Thr Ala Thr Lys Ser Gly Glu Val Phe Thr Pro Pro Leu
        355                 360                 365

Cys Leu Asn Val Asn Trp Ala Leu Phe Phe Met Tyr Lys Val Thr Phe
    370                 375                 380

Leu Ile Ile Val Ala Leu Ser
385                 390

<210> SEQ ID NO 9
<211> LENGTH: 13
<212> TYPE: PRT
<213> ORGANISM: Rattus sp.

<400> SEQUENCE: 9

Pro Ile Tyr Ser Phe Ile Gly Gly Glu His Phe Pro Arg
1               5                   10

<210> SEQ ID NO 10
<211> LENGTH: 9
<212> TYPE: PRT
<213> ORGANISM: Rattus sp.

<400> SEQUENCE: 10

Ile Val Glu Pro Asp Thr Glu Ile Lys
1               5

<210> SEQ ID NO 11
<211> LENGTH: 6
```

```
<212> TYPE: PRT
<213> ORGANISM: Rattus sp.

<400> SEQUENCE: 11

Tyr Gly Phe Ser Pro Arg
  1               5

<210> SEQ ID NO 12
<211> LENGTH: 12
<212> TYPE: PRT
<213> ORGANISM: Rattus sp.

<400> SEQUENCE: 12

Ile Lys Glu Val Ala His Val Asn Leu Glu Val Arg
  1               5                  10

<210> SEQ ID NO 13
<211> LENGTH: 8
<212> TYPE: PRT
<213> ORGANISM: Rattus sp.

<400> SEQUENCE: 13

Val Ala Ala Gly Asp Ser Ala Thr
  1               5

<210> SEQ ID NO 14
<211> LENGTH: 107
<212> TYPE: PRT
<213> ORGANISM: Unknown Organism
<220> FEATURE:
<223> OTHER INFORMATION: Description of Unknown Organism: Mus sp. or
      Homo sapiens

<400> SEQUENCE: 14

Asp Glu Leu Gln Val Ile Gln Pro Glu Lys Ser Val Ser Val Ala Ala
  1               5                  10                  15

Gly Glu Ser Ala Thr Leu Arg Cys Ala Met Thr Ser Leu Ile Pro Val
                 20                  25                  30

Gly Pro Ile Met Trp Phe Arg Gly Ala Gly Ala Gly Arg Glu Leu Ile
             35                  40                  45

Tyr Asn Gln Lys Glu Gly His Phe Pro Arg Val Thr Thr Val Ser Glu
         50                  55                  60

Leu Thr Lys Arg Asn Asn Leu Asp Phe Ser Ile Ser Ile Ser Asn Ile
 65                  70                  75                  80

Thr Pro Ala Asp Ala Gly Thr Tyr Tyr Cys Val Lys Phe Arg Glu Gly
                 85                  90                  95

Ser Pro Asp Val Glu Phe Lys Ser Gly Ala
                100                 105

<210> SEQ ID NO 15
<211> LENGTH: 107
<212> TYPE: PRT
<213> ORGANISM: Unknown Organism
<220> FEATURE:
<223> OTHER INFORMATION: Description of Unknown Organism: Mus sp. or
      Homo sapiens

<400> SEQUENCE: 15

Asp Glu Leu Gln Val Ile Gln Pro Glu Lys Ser Val Ser Val Ala Ala
  1               5                  10                  15

Gly Glu Ser Ala Thr Leu Arg Cys Ala Met Thr Ser Leu Ile Pro Val
                 20                  25                  30
```

-continued

Gly Pro Ile Met Trp Phe Arg Gly Ala Gly Ala Gly Arg Glu Leu Ile
            35                  40                  45

Tyr Asn Gln Lys Glu Gly His Phe Pro Arg Val Thr Thr Val Ser Glu
    50                  55                  60

Leu Thr Lys Arg Asn Asn Leu Asp Phe Ser Ile Ser Ile Ser Asn Ile
65                  70                  75                  80

Thr Pro Ala Asp Ala Gly Thr Tyr Tyr Cys Val Lys Phe Arg Lys Gly
                85                  90                  95

Ser Pro Asp Asp Val Glu Phe Lys Ser Gly Ala
            100                 105

<210> SEQ ID NO 16
<211> LENGTH: 107
<212> TYPE: PRT
<213> ORGANISM: Unknown Organism
<220> FEATURE:
<223> OTHER INFORMATION: Description of Unknown Organism: Mus sp. or
      Homo sapiens

<400> SEQUENCE: 16

Glu Glu Leu Gln Val Ile Gln Pro Glu Lys Ser Val Leu Val Ala Ala
1               5                   10                  15

Gly Glu Thr Ala Thr Leu Arg Cys Thr Ala Thr Ser Leu Ile Pro Val
            20                  25                  30

Gly Pro Ile Met Trp Phe Arg Gly Ala Gly Ala Gly Arg Glu Leu Ile
            35                  40                  45

Tyr Asn Gln Lys Glu Gly His Phe Pro Arg Val Thr Thr Val Ser Asp
    50                  55                  60

Leu Thr Lys Arg Asn Asn Met Asp Phe Ser Ile Arg Ile Gly Asn Ile
65                  70                  75                  80

Thr Pro Ala Asp Ala Gly Thr Tyr Tyr Cys Val Lys Phe Arg Lys Gly
                85                  90                  95

Ser Pro Asp Asp Val Glu Phe Lys Ser Gly Ala
            100                 105

<210> SEQ ID NO 17
<211> LENGTH: 107
<212> TYPE: PRT
<213> ORGANISM: Unknown Organism
<220> FEATURE:
<223> OTHER INFORMATION: Description of Unknown Organism: Mus sp. or
      Homo sapiens

<400> SEQUENCE: 17

Glu Glu Leu Gln Val Ile Gln Pro Asp Lys Ser Val Ser Val Ala Pro
1               5                   10                  15

Gly Glu Ser Ala Ile Leu His Cys Thr Val Thr Ser Leu Ile Pro Val
            20                  25                  30

Gly Pro Ile Gln Trp Phe Arg Gly Ala Gly Pro Ala Arg Glu Leu Ile
            35                  40                  45

Tyr Asn Gln Lys Glu Gly His Phe Pro Arg Val Thr Thr Val Ser Glu
    50                  55                  60

Ser Thr Lys Arg Glu Asn Met Asn Phe Ser Ile Ser Ile Ser Asn Ile
65                  70                  75                  80

Thr Pro Ala Asp Ala Gly Thr Tyr Tyr Cys Val Lys Phe Arg Lys Gly
                85                  90                  95

Ser Pro Asp Asp Val Glu Phe Lys Ser Gly Ala
            100                 105

```
<210> SEQ ID NO 18
<211> LENGTH: 107
<212> TYPE: PRT
<213> ORGANISM: Unknown Organism
<220> FEATURE:
<223> OTHER INFORMATION: Description of Unknown Organism:  Mus sp. or
      Homo sapiens

<400> SEQUENCE: 18

Asp Glu Leu Gln Val Ile Gln Pro Asp Lys Ser Val Ser Val Ala Ala
  1               5                  10                  15

Gly Glu Ser Ala Thr Leu Arg Cys Ala Met Thr Ser Leu Ile Pro Val
                 20                  25                  30

Gly Pro Ile Met Trp Phe Arg Gly Ala Gly Ala Gly Arg Glu Leu Ile
             35                  40                  45

Ser Asn Gln Lys Glu Gly His Phe Pro Arg Val Thr Thr Val Ser Glu
         50                  55                  60

Ser Thr Lys Arg Glu Asn Met Asp Phe Ser Ile Ser Ile Ser Asn Ile
 65                  70                  75                  80

Thr Pro Ala Asp Ala Gly Thr Tyr Tyr Cys Val Lys Phe Arg Lys Gly
                 85                  90                  95

Ser Pro Asp Asp Val Glu Phe Lys Ser Gly Ala
                100                 105

<210> SEQ ID NO 19
<211> LENGTH: 107
<212> TYPE: PRT
<213> ORGANISM: Unknown Organism
<220> FEATURE:
<223> OTHER INFORMATION: Description of Unknown Organism:  Mus sp. or
      Homo sapiens

<400> SEQUENCE: 19

Asp Glu Leu Gln Val Ile Gln Pro Glu Lys Ser Val Ser Val Ala Pro
  1               5                  10                  15

Gly Glu Ser Ala Thr Leu Arg Cys Ala Met Thr Ser Leu Ile Pro Val
                 20                  25                  30

Gly Pro Ile Met Trp Phe Arg Gly Ala Gly Ala Gly Arg Glu Leu Ile
             35                  40                  45

Ser Asn Gln Lys Glu Gly His Phe Pro Arg Val Thr Thr Val Ser Glu
         50                  55                  60

Leu Thr Lys Arg Asn Asn Leu Asp Phe Ser Ile Ser Ile Ser Asn Ile
 65                  70                  75                  80

Thr Pro Ala Asp Ala Gly Thr Tyr Tyr Cys Val Lys Phe Arg Lys Gly
                 85                  90                  95

Ser Pro Asp Asp Val Glu Phe Lys Ser Gly Ala
                100                 105

<210> SEQ ID NO 20
<211> LENGTH: 106
<212> TYPE: PRT
<213> ORGANISM: Unknown Organism
<220> FEATURE:
<223> OTHER INFORMATION: Description of Unknown Organism:  Mus sp. or
      Homo sapiens

<400> SEQUENCE: 20

Glu Glu Leu Gln Val Ile Gln Pro Asp Lys Ser Val Ser Val Ala Pro
  1               5                  10                  15

Gly Glu Ser Ala Ile Leu His Cys Thr Val Thr Ser Leu Ile Pro Val
```

```
                    20                  25                  30

Gly Pro Ile Gln Trp Phe Arg Gly Ala Gly Pro Ala Arg Glu Leu Ile
                35                  40                  45

Tyr Asn Gln Lys Glu Gly His Phe Pro Arg Val Thr Thr Val Ser Asp
         50                  55                  60

Leu Thr Lys Arg Asn Asn Leu Asp Phe Ser Ile Ser Ile Ser Asn Ile
 65                  70                  75                  80

Thr Pro Ala Asp Ala Gly Thr Tyr Tyr Cys Val Lys Phe Arg Lys Gly
                 85                  90                  95

Ser Pro Asp Val Glu Phe Lys Ser Gly Ala
                100                 105

<210> SEQ ID NO 21
<211> LENGTH: 106
<212> TYPE: PRT
<213> ORGANISM: Unknown Organism
<220> FEATURE:
<223> OTHER INFORMATION: Description of Unknown Organism:  Mus sp. or
      Homo sapiens

<400> SEQUENCE: 21

Glu Glu Leu Gln Val Ile Gln Pro Asp Lys Ser Val Ser Val Ala Pro
 1               5                  10                  15

Gly Glu Ser Ala Ile Leu His Cys Thr Val Thr Ser Leu Ile Pro Val
                20                  25                  30

Gly Pro Ile Gln Trp Phe Arg Gly Ala Gly Pro Ala Arg Glu Leu Ile
                35                  40                  45

Tyr Asn Gln Lys Glu Gly His Phe Pro Arg Val Thr Thr Val Ser Glu
         50                  55                  60

Ser Thr Lys Arg Glu Asn Leu Asp Phe Ser Ile Ser Ile Ser Asn Ile
 65                  70                  75                  80

Thr Pro Ala Asp Ala Gly Thr Tyr Tyr Cys Val Lys Phe Arg Lys Gly
                 85                  90                  95

Ser Pro Asp Val Glu Phe Lys Ser Gly Ala
                100                 105

<210> SEQ ID NO 22
<211> LENGTH: 107
<212> TYPE: PRT
<213> ORGANISM: Unknown Organism
<220> FEATURE:
<223> OTHER INFORMATION: Description of Unknown Organism:  Mus sp. or
      Homo sapiens

<400> SEQUENCE: 22

Asp Glu Leu Gln Val Ile Gln Ser Glu Lys Ser Val Ser Val Ala Ala
 1               5                  10                  15

Gly Glu Ser Ala Ala Leu His Cys Ala Met Thr Ser Leu Ile Pro Val
                20                  25                  30

Gly Pro Ile Met Trp Phe Arg Gly Ala Gly Ala Gly Arg Glu Leu Ile
                35                  40                  45

Tyr Asn Gln Lys Glu Gly His Phe Pro Arg Val Thr Thr Val Ser Glu
         50                  55                  60

Leu Thr Lys Arg Asn Asn Leu Asp Phe Ser Ile Ser Ile Ser Asn Ile
 65                  70                  75                  80

Thr Pro Ala Asp Ala Gly Thr Tyr Tyr Cys Val Lys Phe Arg Lys Gly
                 85                  90                  95

Ser Pro Asp Asp Val Glu Phe Lys Ser Gly Ala
```

-continued

```
                100                 105

<210> SEQ ID NO 23
<211> LENGTH: 107
<212> TYPE: PRT
<213> ORGANISM: Unknown Organism
<220> FEATURE:
<223> OTHER INFORMATION: Description of Unknown Organism:  Mus sp. or
      Homo sapiens

<400> SEQUENCE: 23

Asp Glu Leu Gln Val Ile Gln Pro Glu Lys Ser Val Ser Val Ala Ala
 1               5                  10                  15

Gly Glu Ser Ala Thr Leu Arg Cys Ala Met Thr Ser Leu Ile Pro Val
                20                  25                  30

Gly Pro Ile Met Trp Phe Arg Gly Ala Gly Ala Gly Arg Glu Leu Ile
            35                  40                  45

Tyr Asn Gln Lys Glu Gly His Phe Pro Arg Val Thr Thr Val Ser Glu
 50                  55                  60

Leu Thr Lys Arg Asn Asn Leu Asp Phe Ser Ile Arg Ile Ser Asn Ile
65                  70                  75                  80

Thr Pro Ala Asp Ala Gly Thr Tyr Tyr Cys Val Lys Phe Arg Lys Gly
                85                  90                  95

Ser Pro Asp Asp Val Glu Phe Lys Ser Gly Ala
                100                 105

<210> SEQ ID NO 24
<211> LENGTH: 107
<212> TYPE: PRT
<213> ORGANISM: Unknown Organism
<220> FEATURE:
<223> OTHER INFORMATION: Description of Unknown Organism:  Mus sp. or
      Homo sapiens

<400> SEQUENCE: 24

Asp Glu Leu Gln Val Ile Gln Pro Glu Ala Phe Val Ser Val Ala Ala
 1               5                  10                  15

Gly Glu Met Ala Thr Leu Asn Cys Thr Val Thr Ser Leu Leu Pro Val
                20                  25                  30

Gly Pro Ile Gln Trp Phe Arg Gly Ala Cys Pro Gly Gln Lys Leu Ile
            35                  40                  45

Tyr Ser Pro Lys Arg Cys His Ser Pro Arg Val Thr Thr Ile Ser Asp
 50                  55                  60

Gln Arg Lys Arg Asn Ser Thr Asp Tyr Ser Ile Arg Ile Ser Ser Ile
65                  70                  75                  80

Thr Leu Glu Asp Ala Gly Thr Tyr Tyr Cys Met Lys Leu Arg Arg Ala
                85                  90                  95

Ile Pro Ala Asn Val Glu Ile Lys Ser Gly Thr
                100                 105

<210> SEQ ID NO 25
<211> LENGTH: 107
<212> TYPE: PRT
<213> ORGANISM: Unknown Organism
<220> FEATURE:
<223> OTHER INFORMATION: Description of Unknown Organism:  Mus sp. or
      Homo sapiens

<400> SEQUENCE: 25

Glu Glu Leu Gln Met Ile Gln Pro Glu Lys Leu Leu Leu Val Thr Val
 1               5                  10                  15
```

```
Gly Lys Thr Ala Thr Leu His Cys Thr Val Thr Ser Leu Leu Pro Val
                20                  25                  30

Gly Pro Val Leu Trp Phe Arg Gly Val Gly Pro Gly Arg Glu Leu Ile
            35                  40                  45

Tyr Asn Gln Lys Glu Gly His Phe Pro Arg Val Thr Arg Val Ser Asp
        50                  55                  60

Leu Thr Lys Arg Asn Asn Met Asp Phe Ser Ile Arg Ile Ser Ser Ile
65                      70                  75                  80

Thr Pro Ala Val Val Gly Thr Tyr Tyr Cys Val Lys Phe Arg Lys Gly
                85                  90                  95

Ser Pro Glu Asn Val Glu Phe Lys Ser Gly Pro
            100                 105

<210> SEQ ID NO 26
<211> LENGTH: 106
<212> TYPE: PRT
<213> ORGANISM: Unknown Organism
<220> FEATURE:
<223> OTHER INFORMATION: Description of Unknown Organism:  Mus sp. or
      Homo sapiens

<400> SEQUENCE: 26

Glu Glu Leu Gln Val Ile Gln Pro Glu Lys Ser Val Ser Val Ala Ala
1               5                   10                  15

Gly Glu Ser Ala Ala Leu Gln Cys Thr Val Thr Ser Leu Asn Pro Val
                20                  25                  30

Gly Pro Ile Gln Arg Phe Arg Gly Ala Gly Pro Gly Arg Lys Leu Ile
            35                  40                  45

Tyr His Gln Lys Glu Gly His Phe Pro Arg Val Thr Thr Val Ser Asp
        50                  55                  60

Leu Thr Lys Arg Thr Asn Met Asp Phe Ser Ile Cys Ile Ser Asn Ile
65                      70                  75                  80

Thr Pro Ala Asp Ala Gly Thr Tyr Tyr Cys Val Lys Phe Gln Lys Gly
                85                  90                  95

Ser Pro Asp Val Glu Leu Lys Ser Gly Ala
            100                 105
```